US008830450B2

(12) United States Patent
Bond et al.

(10) Patent No.: US 8,830,450 B2
(45) Date of Patent: Sep. 9, 2014

(54) METHODS AND SYSTEMS FOR RAMAN AND OPTICAL CROSS-INTERROGATION IN FLOW-THROUGH SILICON MEMBRANES

(75) Inventors: Tiziana C. Bond, Livermore, CA (US); Sonia E. Letant, Livermore, CA (US)

(73) Assignee: Lawrence Livermore National Security, LLC, Livermore, CA (US)

( * ) Notice: Subject to any disclaimer, the term of this patent is extended or adjusted under 35 U.S.C. 154(b) by 259 days.

(21) Appl. No.: 12/958,302

(22) Filed: Dec. 1, 2010

(65) Prior Publication Data

US 2011/0128537 A1  Jun. 2, 2011

Related U.S. Application Data

(60) Provisional application No. 61/266,017, filed on Dec. 2, 2009.

(51) Int. Cl.
*G01N 21/00* (2006.01)
*G01J 3/44* (2006.01)
*G02B 6/122* (2006.01)
*B82Y 20/00* (2011.01)
*G01N 21/65* (2006.01)
*G02B 6/10* (2006.01)
*G02B 6/12* (2006.01)
*G01N 21/77* (2006.01)

(52) U.S. Cl.
CPC ............ *G01N 21/658* (2013.01); *G02B 6/1225* (2013.01); *B82Y 20/00* (2013.01); *G02B 2006/12176* (2013.01); *G02B 2006/12061* (2013.01); *G02B 6/107* (2013.01); *G01N 21/774* (2013.01)
USPC .............................. 356/73; 356/301; 356/436

(58) Field of Classification Search
CPC ...................................................... G01N 21/658
USPC ................................................ 356/301, 73, 436
See application file for complete search history.

(56) References Cited

U.S. PATENT DOCUMENTS

| | | | | |
|---|---|---|---|---|
| 3,751,992 | A * | 8/1973 | Morgan | ................. 73/863.83 |
| 5,311,426 | A * | 5/1994 | Donohue et al. | ................ 73/1.02 |
| 5,866,430 | A | 2/1999 | Grow | |
| 6,468,823 | B1 | 10/2002 | Scherer et al. | |
| 6,643,439 | B2 | 11/2003 | Notomi et al. | |
| 6,710,879 | B1 | 3/2004 | Hansen et al. | |
| 6,738,551 | B2 | 5/2004 | Noda et al. | |
| 6,785,432 | B2 | 8/2004 | Letant et al. | |

(Continued)

OTHER PUBLICATIONS

Leo L. Chan et al., "Self-referenced assay method for photonic crystal biosensors: Application to small molecule analytes" Sensors and Actuators B 120, 2007, pp. 392-398.

(Continued)

*Primary Examiner* — Kara E Geisel
*Assistant Examiner* — Rufus Phillips
(74) *Attorney, Agent, or Firm* — Steinfl & Bruno, LLP

(57) ABSTRACT

Cross-interrogating photonic detection systems and methods are shown. A flow through photonic crystal membrane with a surface enhanced Raman scattering (SERS) substrate is provided with pores which are distributed along multiple regions. The pores of one region have walls to which a first type of target specific anchor can be attached, while pores of another region have walls to which a second type of target specific anchor can be attached. An optical arrangement out-of-plane to the SERS substrate is also provided for enhanced sensitivity and identification of target organisms.

25 Claims, 15 Drawing Sheets

(56) References Cited

U.S. PATENT DOCUMENTS

| | | | |
|---|---|---|---|
| 6,867,900 B2* | 3/2005 | Weisbuch et al. | 359/321 |
| 7,026,640 B2 | 4/2006 | Nathan et al. | |
| 7,027,676 B2* | 4/2006 | VanWiggeren et al. | 385/14 |
| 7,155,076 B2 | 12/2006 | Letant et al. | |
| 7,206,488 B1 | 4/2007 | Altug et al. | |
| 7,289,221 B2 | 10/2007 | Wang et al. | |
| 7,318,907 B2* | 1/2008 | Stark et al. | 422/50 |
| 7,351,588 B2* | 4/2008 | Poponin | 436/171 |
| 7,388,661 B2 | 6/2008 | Li et al. | |
| 7,476,787 B2 | 1/2009 | Thomas et al. | |
| 7,492,979 B2 | 2/2009 | Wang et al. | |
| 8,187,481 B1 | 5/2012 | Hobbs | |
| 2003/0143580 A1 | 7/2003 | Straus | |
| 2004/0021193 A1 | 2/2004 | Nathan et al. | |
| 2004/0067163 A1 | 4/2004 | Prasad et al. | |
| 2005/0084980 A1* | 4/2005 | Koo et al. | 436/171 |
| 2005/0206895 A1* | 9/2005 | Salmelainen | 356/318 |
| 2006/0072642 A1 | 4/2006 | Wang et al. | |
| 2009/0244532 A1 | 10/2009 | Letant et al. | |
| 2011/0128536 A1 | 6/2011 | Bond et al. | |

OTHER PUBLICATIONS

E. Chow et al., "Ultracompact biochemical sensor built with two-dimensional photonic crystal microcavity" Optics Letters, vol. 29, No. 10, 2004, pp. 1093-1095.

Bradley R. Hart et al., "New method for attachment of biomolecule to porous silicon", Chem. Commun., 2003, pp. 322-323.

Mindy R. Lee et al., "Nanoscale microcavity sensor for single particle detection", Optics Letters, vol. 32, 2007, pp. 3284-3286.

Sonia E. Letant et al., "Enzyme Immobilization on Porous Silicon Surfaces", Adv. Mater., 16, 2004, pp. 689-693.

Sonia Letant et al., "Functionalized silicon membranes for selective bio-organism capture", Nature Materials, vol. 2, 2003, pp. 391-395.

Levine, M.J. et al., "Zero mode waveguides for single molecule analysis at high concentration", Science, 299, 2003, pp. 682-686.

Victor S.-Y. Lin et al., "A Porous Silicon-Based Optical Interferometric Biosensor", Science, vol. 278, 1997, pp. 840-843.

Marko Loncar et al., "Photonic crystal laser sources for chemical detection", Applied Physics Letters, vol. 82, 2003, pp. 4648-4650.

F. Morhard et al. "Immobilization of antibodies in micropatterns for cell detection by optical diffraction", Sensors and Actuators B 70, 2000, pp. 232-242.

Selena Chan et al., "Identification of Gram Negative Bacteria Using Nanoscale Silicon Microcavities" J. Am. Chem. Soc. 2001, 123, pp. 11797-11798.

Bradley Schmidt et al., "Nanocavity in a silicon waveguide for ultrasensitive nanoparticle detection", Applied Physics Letters, vol. 85, 2004, pp. 4854-4856.

Nilsson, J., et al., Localized functionalization of single nanopores, Advanced Materials 2006, 18: 427-431.

Larsson, E., et al., Sensing characteristics of NIR localized surface plasmon resonance in gold nanorings for application as ultrasensitive biosensors, Nano Letters 2007, 7: 1256-1263.

S.E. Letant, S. Content, T.T. Tan, F. Zenhausern, and M.J. Sailor (2000), "Integration of Porous Silicon Chips in an Electronic Artificial Nose", Sensors and Actuators, B 69, 193-198.

Non-Final Office Action mailed by the USPTO on Mar. 31, 2011 for U.S. Appl. No. 12/206,337, filed Sep. 8, 2008.

Sarah E. Baker et al. Detection of bio-organism simulants using random binding on a defect-free photonic crystal. Published in Appl. Phys. Lett., vol. 97, Issue 11, 113701 (2010). *Pre-publication version is provided herewith.*

Katz, A., In situ determination of refractive index and size of *Bacillus* spores by light transmission, Optics Letters 2005, 30: 589-591.

Grow, A., et al., New biochip technology for label-free detection of pathogens and their toxins, Journal of Microbiological Methods 2003, 221-233.

Nguyen, B., et al., Membrane-Based Electrochemical Nanobiosensor for the Detection of Virus, Anal. Chem. 2009, 81: 7226-7234.

Dorfner, D., et al., Silicon photonic crystal nanostructures for refractive Index sensing, Applied Physics Letters 2008, 93: 181103-1-181103-3.

Vollmer, F., et al., Single virus detection from the reactive shift of a whispering-gallery mode, PNAS 2008, 105: 20701-20704.

Hagino, H., et al., Effects of fluctuation in air hole radii and positions on optical characteristics in photonic crystal heterostructure nanocavities, Physical Review B 2009, 79: 085112-1-085112-8.

Rea, I., et al., Fabrication and characterization of a porous silicon based microarray for label-free optical monitoring of biomolecular interactions, Journal of Applied Physics 2010, 107: 014513-1-014513-4.

Guicheteau, J., et al., *Bacillus* Spore Classification via Surface-Enhanced Raman Spectroscopy and Principal Component Analysis, Applied Spectroscopy 2008, 62: 267-272.

Lee, J., Real-time detection of airborne viruses on a mass-sensitive device, Applied Physics Letters 2008, 93: 013901-1-013901-3.

Fitch, J., et al., Technology Challenges in Responding to Biological or Chemical Attacks in the Civilian Sector, Science 2003, 302: 1350-1354.

Hodges, L., et al., National validation study of a swab protocol for the recovery of *Bacillus anthracis* spores from surfaces, Journal of Microbiological Methods 2010, 141-146.

Cyrklaff, M., et al., Cryo-electron tomography of vaccinia virus, PNAS 2005, 102: 2772-2777.

Schwartz, M., et al., The Smart Petri Dish: A Nanostructured Photonic Crystal for Real-Time Monitoring of Living Cells, Langmuir 2006, 22: 7084-7090.

Buttner, M., et al., Determination of the Efficacy of Two Building Decontamination Strategies by Surface Sampling with Culture and Quantitative PCR Analysis, Applied and Environmental Microbiology 2004, 70: 4740-4747.

Lee, M., et al., Nanoscale microcavity sensor for single particle detection, Optics Letters 2007, 32: 3284-3286.

Mortensen, N., et al., Liquid-infiltrated photonic crystals: enhanced light-matter interactions for lab-on-a-chip applications, Microfluid Nanofluid 2008, 4: 117-127.

Skottrup, P., et al., Towards on-site pathogen detection using antibody-based sensors, Biosensors and Bioelectronics 2008, 24: 339-348.

Golightly, R., et al., Surface-Enhanced Raman Spectroscopy and Homeland Security: A Perfect Match?, AC Nano 2009, 3: 2859-2869.

van der Heijden, R., et al., InP-based two-dimensional photonic crystals filled with polymers, Applied Physics Letters 2006, 88: 161112-1-161112-3.

Buswell, SC, et al., Specific detection of proteins using photonic crystal waveguides, Optics Express 2008, 16: 15949-15957.

Lee, S., et al., Improved Localized Surface Plasmon Resonance Immunoassay with Gold Bipyramid Substrates, Anal. Chem. 2009, 81: 4450-4455.

Letant, SE, et al., Most-Probable-Number Rapid Viability PCR method to detect viable spores of *Bacillus anthracis* in swab samples, Journal of Microbiological Methods 2010, 81: 200-202.

Kane, SR, et al., Rapid, high-throughput, culture-based PCR methods to analyze samples for viable spores of *Bacillus anthracis* and its surrogates, Journal of Microbiological Methods 2009, 278-284.

Lin, S., et al., Design of nanoslotted photonic crystal waveguide cavities for single nanoparticle trapping and detection, Optics Letters 2009, 34: 3451-3453.

Alexander, T., et al., Characterization of a commercialized SERS-active substrate and its application to the identification of intact *Bacillus* endospores, Applied Optics 2007, 46: 3878-3890.

Asano, T., et al., Analysis of the experimental Q factors (~1 million) of photonic crystal nanocavities, Optics Express 2006, 14: 1996-2002.

Notice of Allowance mailed by the USPTO on Jul. 14, 2011 for U.S. Appl. No. 12/206,337, filed Sep. 8, 2008 in the name of Lawrence Livermore.

Andrade, G., et al., Multilayer silver nanoparticles-modified optical fiber tip for high performance SERS remote sensing, Biosensors & Bioelect. 2010, 25: 2770-2275.

(56) References Cited

OTHER PUBLICATIONS

Averitt, RD, et al., Plasmon Resonance Shifts of Au-Coated Au2S Nanoshells: Insight into Multicomponent Nanoparticle Growth, Phys. Rev. Let. 1997, 78: 4217-4220.

Chang, A., et al., Nanopillars array for surface enhanced Raman scattering, Adv. Environ. Chem. & Biol. Sensing Tech. 2010, 8024: 1-8.

Campion, A., et al., Surface-enhanced Raman scattering, Chem. Soc. Rev. 1998, 27: 241-250.

Carron, K., et al., Molecular-Specific Chromatographic Detector Using Modified SERS Substrates, Anal. Chem. 1995, 67: 3353-3356.

Dahlin, A., et al., Localized Surface Plasmon Resonance Sensing of Lipid-Membrane-Mediated Biorecognition Events, JACS 2005, 127: 5043-5048.

Dhawan, A, et al., Fabrication of nanodot plasmonic waveguide structures using FIB milling and electron beam-induced deposition, Scanning 2009, 31: 139-146.

Dmitriev, A., et al., Gold—Silica—Gold Nanosandwiches: Tunable Bimodal Plasmonic Resonators, Small 2007, 3: 294-299.

Draine, B., The discrete-dipole approximation and its application to interstellar graphite grains, The Astrophys. Journal 1988, 333: 848-872.

Elghanian R., et al., Selective Colorimetric Detection of Polynucleotides Based on the Distance-Dependent Optical Properties of Gold Nanoparticles, Science 1997, 277: 1078-1081.

El-Sayed, I., et al., Surface Plasmon Resonance Scattering and Absorption of anti-EGFR Antibody Conjugated Gold Nanoparticles in Cancer Diagnostics: Applications in\Oral Cancer, Nano Letters 2005, 5: 829-834.

Feng, S., et al., Fiber coupled waveguide grating structures, Appl. Phys. Lett. 2010, 96: 133101-1-133101-3.

Fleischmann, M. et al., Raman spectra of pyridine assorbed at a silver electrode, Chem. Phys. Lett. 1974, 26: 163 166.

Gu, C., et al., Fiber Sensors for Molecular Detection, Info Optics & Optical Data Storage 2010, 7851: 785105-785105-14.

Guieu, V., et al., Remote surface enhanced Raman spectroscopy imaging via a nanostructured optical fiber Bundle, Optical Society of America 2009, 17: 24030-24035.

Gunnarsson, L., et al., Confined Plasmons in Nanofabricated Single Silver Particle Pairs: Experimental Observations of Strong Interparticle Interactions, J. Phys. Chem. B 2005, 109: 1079-1087.

Gutes, A., et al., Silver Nanostructures on Silicon Based on Galvanic Displacement Process, J. Phys. Chem. C 2009, 113: 16939-16944.

Haes, A., et al., A Nanoscale Optical Biosensor: Sensitivity and Selectivity of an Approach Based on the Localized Surface Plasmon Resonance Spectroscopy of Triangular Silver Nanoparticles, JACS 2002, 124: 10596-10604.

Haes, A., et al., A Localized Surface Plasmon Resonance Biosensor: First Steps toward an Assay for Alzheimer's Disease, Nano Letters 2004, 4: 1029-1034.

Hanarp, P., et al., Optical Properties of Short Range Ordered Arrays of Nanometer Gold Disks Prepared by Colloidal Lithography, J. Phys. Chem. B 2003, 107: 5768-5772.

Hanarp, P., et al., Nanostructured model biomaterial surfaces prepared by colloidal lithography, Nanostructured Materials 1999, 12: 429-432.

Hutter, E., et al., Exploitation of localized surface plasmon resonance, Adv. Mat. 2004, 16: 1685-1706.

Jansen, T., et al., Nanosphere Lithography: Effect of the External Dielectric Medium on the Surface Plasmon Resonance Spectrum of a Periodic Array of Silver Nanoparticles, J. Phys. Chem. B 1999, 103: 9846-9853.

Jansen, T., et al., Nanosphere Lithography: Surface Plasmon Resonance Spectrum of a Periodic Array of Silver Nanoparticles by Ultraviolet-Visible Extinction Spectroscopy and Electrodynamic Modeling, J. Phys. Chem. B 1999, 103: 2394-2401.

Jung, L., et al., Quantitative Interpretation of the Response of Surface Plasmon Resonance Sensors to Adsorbed Films, Langmuir 1998, 14: 5636-5648.

Kim, S., et al., Patterned Arrays of Au Rings for Localized Surface Plasmon Resonance, Langmuir 2006, 22: 7109-7112.

Kim, A., et al., Study of Molecular Trapping Inside Gold Nanofinger Arrays on Surface-Enhanced Raman Substrates, JACS 2011, 133: 8234-8239.

Kniepp, K., et al., Single Molecule Detection Using Surface-Enhanced Raman Scattering (SERS), Phys. Rev. Lett. 1997, 78: 1667-1670.

Kniepp, K., et al., Surface-enhanced Raman scattering and biophysics, J. Phys.: Condensed Matter 2002, 14: R597-R624.

Kostovski, G., et al., Nanoimprinted optical fibres: Biotemplated nanostructures for SERS sensing, Biosesnors & Bioelectronics 2009, 24: 1531-1535.

Langhammer, C., et al., Plasmonic Properties of Supported Pt and Pd Nanostructures, Nano Letters 2006, 6: 833-838.

Lucotti, A., et al., Fiber-optic SERS sensor with optimized geometry, Sensors & Actuators 2007, 121: 356-364.

Malinsky, M., et al., Chain Length Dependence and Sensing Capabilities of the Localized Surface Plasmon Resonance of Silver Nanoparticles Chemically Modified with Alkanethiol Self-Assembled Monolayers, J. Am. Chem. Soc. 2001, 123: 1471-1482.

McFarland, A., et al., Single Silver Nanoparticles as Real-Time Optical Sensors with Zeptomole Sensitivity, Nano Letters 2003, 3: 1057-1062.

Miller, M., et al., Sensitivity of Metal Nanoparticle Surface Plasmon Resonance to the Dielectric Environment, J. Phys. Chem. B 2005, 109: 21556-21565.

Mock, J., et al., Local Refractive Index Dependence of Plasmon Resonance Spectra from Individual Nanoparticles, Nano Letters 2003, 3: 485-491.

Morokoshi, S., et al., Sensing Capabilities of Colloidal Gold Modified with a Self-Assembled Monolayer of a Glucose-Carrying Polymer Chain on a Glass Substrate, Langmuir 2004, 20: 8897-8902.

Mullen, K., et al., Surface-Enhanced Raman Spectroscopy with Abrasively Modified Fiber Optic Probes, Am. Chem. Soc. 1991, 63: 2196-2199.

Nath, N., et al., A Colorimetric Gold Nanoparticle Sensor to Interrogate Biomolecular Interactions in Real Time on a Surface, Anal. Chem. 2002, 74: 504-509.

Nehl, C., et al., Optical Properties of Star-Shaped Gold Nanoparticles, Nano Letters 2006, 6: 683-688.

Nie, S., et al., Probing Single Molecules and Single Nanoparticles by Surface-Enhanced Raman Scattering, Science 1997, 275: 1102-1106.

Okamoto, T., et al., Local plasmon sensor with gold colloid monolayers deposited upon glass substrates, Optics Letters 2000, 25: 372-374.

Olofsson, L., et al., Surface-Based Gold-Nanoparticle Sensor for Specific and Quantitative DNA Hybridization Detection, Langmuir 2003, 19: 10414-10419.

Ozbay, E., Plasmonics: Merging Photonics and Electronics at Nanoscale Dimensions, Science 2006, 311: 189-193.

Prikulis, J., et al., Optical Spectroscopy of Nanometric Holes in Thin Gold Films, Nano Letters 2004, 4: 1003-1007.

Purcell, E., et al., Scattering and absorption of light by non-spherical dielectric grains, The Astrophysical Journal 1973, 186: 705-714.

Raschke, G., et al., Biomolecular Recognition Based on Single Gold Nanoparticle Light Scattering, Nano Letters 2003, 3: 935-938.

Reinhard, B., et al., Calibration of Dynamic Molecular Rulers Based on Plasmon Coupling between Gold Nanoparticles, Nano Letters 2005, 5: 2246-2252.

Rindzevicius, T., et al., Plasmonic Sensing Characteristics of Single Nanometric Holes, Nano Letters 2005, 5: 2335-2339.

Schelm, S., et al., Internal Electric Field Densities of Metal Nanoshells, J. Phys. Chem. B 2005, 109: 1689-1694.

Shanmukh, S., et al., Rapid and Sensitive Detection of Respiratory Virus Molecular Signatures Using a Silver Nanorod Array SERS Substrate, Nano Letters 2006, 6: 2630-2636.

Sherry, L., et al., Localized Surface Plasmon Resonance Spectroscopy of Single Silver Triangular Nanoprisms, Nano Letters 2006, 6: 2060-2065.

(56) References Cited

OTHER PUBLICATIONS

Shi, J., et al., Optical characterization of electronic transitions arising from the Au/S interface of self-assembled n-alkanethiolate monolayers, Chem. Phys. Lett. 1995, 246: 90-94.
Shumaker-Parry, J., et al., Fabrication of crescent-shaped optical antennas, Adv. Mat. 2005, 17: 2131-2134.
Sönnichsen, C. et al., Spectroscopy of single metallic nanoparticles using total internal reflection microscopy, Appl. Phys. Lett. 2000, 77: 2949-2951.
Sun, Y., et al., Increased Sensitivity of Surface Plasmon Resonance of Gold Nanoshells Compared to That of Gold Solid Colloids in Response to Environmental Changes, Anal. Chem. 2002, 74: 5297-5305.
Svedhem, S., et al., Patterns of DNA-Labeled and scFv-Antibody-Carrying Lipid Vesicles Directed by Material-Specific Immobilization of DNA and Supported Lipid Bilayer Formation on an Au/SiO2 Template, ChemBioChem 2003, 4: 339-343.
Symthe, E., et al., Optical Antenna Arrays on a Fiber Facet for in Situ Surface-Enhanced Raman Scattering Detection, Nano Letters 2009, 9: 1132-1138.
Tam, F., et al., Geometrical Parameters Controlling Sensitivity of Nanoshell Plasmon Resonances to Changes in Dielectric Environment, J. Phys. Chem. B 2004, 108: 17290-17294.
Tao, A., et al., Langmuir-Blodgett Silver Nanowire Monolayers for Molecular Sensing Using Surface-Enhanced Raman Spectroscopy, Nano Letters 2003, 3: 1229-1233.
Viets, C., et al., Single-fibre surface-enhanced Raman sensors with angled tips, J. Raman Spectroscopy 2000, 31: 625-631.
Viets, C., et al., Comparison of fibre-optic SERS sensors with differently prepared tips, Sensors & Actuators B 1998, 51: 92-99.
Wang, H., et al., Nanorice: A hybrid plasmonic nanostructure, Nano Letters 2006, 6: 827-832.
Yang, X., et al., Highly Sensitive Detection of Proteins and Bacteria in Aqueous Solution Using Surface-Enhanced Raman Scattering and Optical Fibers, Anal. Chem. 2011, 83: 5888-5894.
Yang, X., et al., High-sensitivity molecular sensing using hollow-core photonic crystal fiber and surface-enhanced Raman scattering, J. Opt. Soc. Am. A 2010, 27: 977-1004.
Yang, X., et al., Portable fiber sensors based on surface-enhanced Raman scattering, Rev. Sci. Instruments 2010, 81: 123103-1-123103-5.
Yang, X., et al., Nanopillar array on a fiber facet for highly sensitive surface-enhanced Raman scattering, Optics Express 2012, 20: 24819-24826.
Yonzon, C., et al., A Comparative Analysis of Localized and Propagating Surface Plasmon Resonance Sensors: The Binding of Concanavalin A to a Monosaccharide Functionalized Self-Assembled Monolayer, JACS 2004, 126: 12669-12676.
Zhu, Y., et al., Development of silver nanorod array based fiber optic probes for SERS detection, Sensors & Actuators B 2011, 157: 42-50.
Aizpurua, J., et al., Optical properties of gold nanorings, Physical Review Letters 2003, 90: 057401-1-057401-4.
Bora, M., et al., Plasmon resonant cavities in vertical nanowire arrays, Nano Letters 2010, 10: 2832-2837.
Etchegoin, P. G., et al., A perspective on single molecule SERS: Current status and future challenges, Physical Chemistry Chemical Physics 2008, 10: 6079-6089.
Gartia, M., et al., Rigorous surface enhanced Raman spectral characterization of large-area high-uniformity silver-coated tapered silica nanopillar arrays, Nanotechnology 2010, 21: 395701-1-395701-9.
Goddard, L., et al., Rapidly reconfigurable all-optical universal logic gates, Proc. of SPIE 2006, 6368: 63680H-1-63680H-13.
Jarvis, R., et al., Discrimination of bacteria using surface-enhanced Raman spectroscopy, Anal. Chem. 2004, 76: 40-47.
Johansson, A., et al., Sampled-grating DBR laser-based analog optical transmitters, Journal of Lightwave Technology 2003, 21: 2968-2976.
Murray, C. A., et al., Silver-molecule separation dependence of surface-enhanced Raman scattering, Physical Review Letters 1981, 46: 57-60.
Nakatsuhara, K., et al., All-optical set-reset operation in a distributed feedback GaInAsP waveguide, IEEE Photonics Technology Letters 1998, 10: 78-80.
Netti, C., et al., Reliable substrate technology for surface enhanced Raman spectroscopy, Raman Technology for Today's Spectroscopists 2005, 3-8.
Pan, G., et al., Optical injection induced polarization bistability in vertical cavity surface emitting lasers, Appl. Phys. Lett. 1993, 63: 2999-3001.
Pocha, M. et al., Gain Lever Characterization in Monolithically Integrated Diode Lasers, Physics & Simulation of Optoelec. Devices 2005, 5772: 288-298.
Tanenaka, M., et al., Realization of All-Optical Flip-Flop Using Directionally Coupled Bistable Laser Diode, IEEE Photo. Tech. Let. 2004, 16: 45-47.
Tanenaka, M., et al., Multimode Interference Bistable Laser Diode, IEEE Photo. Tech. Let. 2003, 15: 1035-1037.
Uenohara, H., et al., Operation characteristics of a side-light-injection multiple quantum well bistable laser for all-optical switching, Jpn. J. Appl. Phys. 1994, 815-821.
Vo-Dinh, T., et al., Cancer gene detection using surface-enhanced Raman scattering (SERS), Journal of Raman Spectroscopy 2002, 33: 511-516.
Wen, P., et al., Observation of bistability in a Vertical-Cavity Semiconductor Optical Amplifier (VCSOA), Optical Society of America 2002, 10: 1273-1278.
Zhou, J., et al., All-optical bistable switching dynamics in 1.55 μm two-segment strained multiquantum-well distributed-feedback lasers, Journal of Lightwave Technology 1997, 15: 342-355.
Fernandez, A., et al., Use of interference lithography to pattern arrays of submicron resist structures for field emission flat panel displays, J. Vac. Sci. Technol. B 1997, 15: 729-735.
Welty, R. J., et al., Integrated laser with low-loss high index-contrast waveguides for OEICs, SPIE, International Symposium on Integrated Optoelectronic Devices, 2004, San Jose 1-14.
Yang, X., et al., Nanopillar array on a fiber facet for highly sensitive surface-enhanced Raman scattering, Optics Express 2012, 20: 24819-24825.
Non-Final Office Action mailed on May 8, 2013 for U.S. Appl. No. 12/957,883, filed Dec. 1, 2010 in the name of Tiziana C. Bond et al.
Final Office Action mailed on Nov. 13, 2013 for U.S. Appl. No. 12/957,883, filed Dec. 1, 2010 in the name of Tiziana C. Bond et al.
Non-Final Office Action mailed on Nov. 27, 2013 for U.S. Appl. No. 13/117,079, filed May 26, 2011 in the name of Sonia Edith Letant et al.

\* cited by examiner

Diamond structure, Si

Schrödinger's equation $$\hat{H}|\psi\rangle = E \cdot |\psi\rangle$$

$$\hat{H} = -\frac{\hbar^2}{2m}\nabla^2 + V(\vec{r})$$

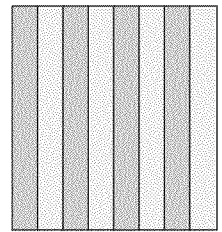
**FIG. 2A
(PRIOR ART)**
Maxwell equations
$$\nabla \times \left[ \frac{1}{\varepsilon(r)} \nabla \times H(r) \right] = \left[ \frac{\omega}{c} \right]^2 H(r)$$
, where $\varepsilon(r) = \varepsilon(r+R)$
**FIG. 2B
(PRIOR ART)**
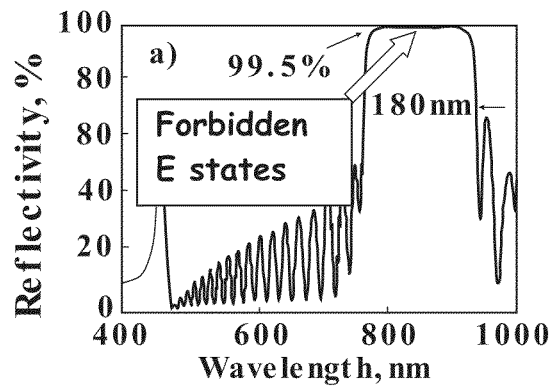
**FIG. 2C
(PRIOR ART)**

METHODS AND SYSTEMS FOR RAMAN AND OPTICAL CROSS-INTERROGATION IN FLOW-THROUGH SILICON MEMBRANES

CROSS REFERENCE TO RELATED APPLICATIONS

The present application claims the priority benefit of U.S. Provisional Application No. 61/266,017 filed on Dec. 2, 2009, which is incorporated herein by reference in its entirety. The present application may be related to U.S. patent application Ser. No. 12/206,337 filed on Sep. 8, 2008, and U.S. Pat. No. 7,155,076 entitled "Target Molecules Detection by Waveguiding in a Photonic Silicon Membrane", both of which are incorporated herein by reference in their entirety.

STATEMENT OF GOVERNMENT GRANT

The United States Government has rights in this invention pursuant to Contract No. DE-AC52-07NA27344 between the United States Department of Energy and Lawrence Livermore National Security, LLC for the operation of Lawrence Livermore National Laboratory.

FIELD

The present disclosure relates to cross-interrogation in photonic membranes. More in particular, it relates methods and systems for Raman and optical cross-interrogation in flow-through silicon membranes.

BACKGROUND

Recently, interest has emerged in label-free optical affinity-based biosensors, which allow study of bio-organisms without fluorescence or radiolabels, and thus dramatically simplify assays. Typically, affinity-based biosensors detect the presence of a target molecule by selective binding to a capture probe. For optical biosensors, binding translates into a change in optical properties, e.g., the complex refractive index or luminescence.

Optical detection methods based on complex refractive index transduction include interferometry in micro and nanofabricated devices, including porous thin films, Bragg reflectors, and microcavities, all of which require an optical measurement system with large beams and sensing areas (about 1 mm$^2$). See E. Chow, A. Grot, L. W. Mirkarimi, M. Sigalas, and G. Girolami, Ultracompact biochemical sensor built with two-dimensional photonic crystal microcavity, Optics Letters 29, 1093 (2004); L. L. Chan, B. T. Cunningham, P. Y. Li, D. Puff, "Self-referenced assay method for photonic crystal biosensors: Application to small molecule analytes", Sens. Actuators B 120, 392 (2007); V. S.-Y. Lin, K. Motesharei, K. Motesharei, K.-P. S. Dancil, M. J. Sailor, and M. R. Ghadiri, Science 278, 840 (1997); F. Morhard, J. Pipper, R. Dahint, and M. Grunze, Sens. Actuators B 70, 232 (2000); M. Loncar, A. Scherer, and Y. Qiu, Appl. Phys. Lett. 82, 4648 (2003).

Within the optical detection methods, photonic crystals constitute an emerging alternative technology due to their powerful light-confinement abilities which would enable local, and sensitive, refractive index measurements.

Extensive work has been performed during the last fifteen years to build and investigate photonic crystals, the optical analogues to electronic semiconductors. In semiconductors, electrons propagate in a periodic potential, which originates from the atomic lattice. This modifies the dispersion of free electrons and opens a band gap in the energy diagram, as shown in FIGS. 1A-1C.

In particular, FIGS. 1A-1C show electron dispersion in semiconductors. FIG. 1A shows a periodic lattice for silicon. FIG. 1B shows the induced periodic potential affecting the allowed electron energy states and shows Schrödinger's equation describing the quantum mechanical properties of electrons in a crystalline solid. FIG. 1C shows how solutions of the equations result in a band gap diagram with two allowed energy bands (valence band and conduction band) separated by a forbidden band (also called an electronic band gap).

Photonic crystals are materials built to present a periodic variation of refractive index. With periodicity being of the same order of magnitude as the wavelength of the electromagnetic (EM) waves, these structures exhibit band gaps for photons, as indicated in FIGS. 2A-2C, where photon dispersion in a 1D photonic crystal is shown. In particular, FIG. 2A shows the 1D periodic permittivity distribution, FIG. 2B shows Maxwell's equation describing the electromagnetic properties of photons in a medium of periodic refractive index, and FIG. 2C shows how solutions of the equation result in the opening of a forbidden band (also called photonic band gap) for the energy states of the photons.

Most of these devices are designed with opto-electronic applications in mind and despite a recent step in the bio-sensing direction with blind 1D structures (see Schmidt, B., Alemeida, V., Manolataou, C., Prebel S., & Lipson, M., "Nanocavity in a silicon waveguide for ultrasensitive detection", Appl. Phys. Lett. 85, 4854 (2004)), and non-specific chemical detection with blind 2D crystals, no selective chemical or biological detection has ever been reported with a 2D photonic platform (see the previously mentioned paper and also Levine, M. J. et al., "Zero-mode waveguides for single molecule analysis at high concentration", Science, 299 (2003)).

The ability to manipulate photonic band gaps in the crystals by design offers the possibility of engineering highly resonant structures, and therefore high-Q microcavities, which makes photonic crystals attractive candidates for ultra compact, highly sensitive assays. Over a few µm$^2$ sensing area, a few fL amount of sample analyte could be studied, providing the backbone for a very dense platform with single organism detection limit (lab-on-chip).

The various schemes and diagrams of FIG. 3 show a 1D photonic bio-sensing platform designed by Fauchet et al. (see M. R. Lee, and P. M. Fauchet, "Nanoscale microcavity sensor for single particle detection", Optics Lett. 32, 3284 (2007)— S. Chan, S. R. Horner, P. M. Fauchet, & B. L. Miller, "Identification of Gram negative bacteria using nanoscale silicon microcavities", J. Am. Chem. Soc. 123, 11797 (2001)).

The top scheme of FIG. 3 describes the device layout in which a 1D photonic structure is electrochemically etched on a silicon wafer. Layers of porous silicon with alternating high and low porosities constitute distributed Bragg reflectors (DBRs) around a luminescent central layer, also called a cavity. The entire assembly rests on the silicon substrate. The data shown in the four center diagrams of FIG. 3 corresponds to the luminescence of a series of cavities filtered by the surrounding DBRs and collected on the top of the device.

The darker lines of the two upper center diagrams are data collected after functionalization of the device with TWCP (tetratryptophan ter-cyclo pentane), a molecule that selectively binds lipid A, present in the viral coat of Gram(−) bacteria. The lighter lines of the two upper center diagrams are data collected after exposure of the functionalized device to Gram(−) bacteria (right) and Gram(+) bacteria (left). The lines of the two lower diagrams represent the difference between the darker and lighter lines discussed above and allow measuring of the spectral shift in photonic band gap resulting from the increase of refractive index in the DBRs upon binding of bacteria. The data is summarized in the bottom table of FIG. 3, indicating that no shift occurred upon exposure to Gram(+) bacteria while a 3-4 nm shift occurred upon exposure to 2 μg of Gram(−) bacteria.

Although the device presented in FIG. 3 can be used as a chemically functionalized 1D photonic crystal for bio-organism detection, the device presented on FIG. 3 requires the binding of a minimum of 2 μg of bacteria (thousands of organisms) to generate a positive signal. Indeed, the detection limit for a porous silicon crystal is inherently high because transduction is generated by a change of effective refractive index that has to occur across the entire volume of the crystal.

Functionalized silicon membranes were fabricated by electrochemistry and their ability demonstrated to selectively capture simulated bio-organisms. A photonic membrane can be defined as a photonic crystal formed of a periodic array of through-holes fabricated in a free-standing membrane waveguide, where the refractive index of the membrane material is larger than the refractive index of the surrounding air or liquid. A photonic membrane provides strong confinement of light both along and perpendicular to the plane of the membrane. In particular, FIG. 4 shows SEM pictures (top view in the background and cross section in the center) of a silicon membrane with 2 μm pores prepared by electrochemistry. This device was chemically functionalized with enzymes and selective capture of enzyme-functionalized beads (see central sphere in the bottom inset) was demonstrated. See Létant, S. E., Hart, B. R., van Buuren, A. W. & Terminello, L. J., "Functionalized silicon membranes for selective bio-organism capture", Nature Materials 2, 391 (2003).

In order to add chemical specificity to size selectivity, nanoporous silicon devices were etched on pre-patterned silicon substrates and covalently functionalized with enzymes (see Létant, S. E., Hart, B. R., Kane, S. R., Hadi, M., Shields, S. M. & Reynolds, J. G., "Enzyme immobilization on porous silicon surfaces", Adv. Mat. 16, 689 (2004) and Hart, B. R., Létant S. E. et al., "New method for attachment of biomolecules to porous silicon", Chem. Comm. 3, 322 (2003)). See also U.S. Pat. No. 7,155,076, incorporated herein by reference in its entirety.

The ability of the functionalized membranes to capture simulated bio-organisms was then successfully tested (as shown in FIG. 4 and in the related paper and patent mentioned above).

SUMMARY

According to a first aspect, a combination photonic detection and identification system comprising, a photonic membrane with through pores, the through pores having inner walls to which chemical or biological target specific anchors are adapted to be attached, a first optical input to the photonic membrane, the first optical input in-plane with the photonic membrane, a first optical output detecting arrangement arranged in-plane with the photonic membrane, a second optical input to the photonic membrane, the second optical input arranged out-of-plane to the photonic membrane, and a second optical output detecting arrangement arranged to the photonic membrane, wherein the photonic membrane is a silicon photonic crystal further comprising a SERS substrate, the SERS substrate being tuned to excite plasmons, wherein the SERS substrate is adapted to couple the second optical input into molecules at or near a surface of the SERS substrate, the coupled second optical input from the molecules releasing photons, and wherein the through pores are distributed on the photonic membrane along multiple regions of through pores, through pores pertaining to a first region having inner walls to which a first type of chemical or biological target specific anchor is attached, through pores pertaining to a second region having inner wall to which a second type of chemical or biological target specific anchor is attached, and so on.

According to a second aspect, a combination photonic detection and identification system comprising a plurality of photonic membranes stacked on each other, each photonic membrane having through pores, the through pores having inner walls to which chemical or biological target specific anchors are adapted to be attached, a first optical input arrangement, the first optical input arrangement in-plane with the plurality of photonic membranes, a first optical output detecting arrangement connected in-plane with the plurality of photonic membranes, a second optical input, the second optical input arranged out-of-plane to the plurality of photonic membranes, and a second optical output arrangement connected out-of-plane to the plurality of photonic membranes, wherein the plurality of photonic membranes are silicon photonic crystals, wherein the plurality of photonic membrane comprises a SERS substrate, the SERS substrate being tuned to excite plasmons, wherein the SERS substrate is adapted to couple the second optical input into molecules at or near a surface of the SERS substrate, the coupled second optical input from the molecules releasing photons, wherein the through pores are distributed on each of the photonic membranes along multiple regions of through pores, through pores pertaining to a first region having inner walls to which a first type of chemical or biological target specific anchor is attached, through pores pertaining to a second region having inner walls to which a second type of chemical or biological target specific anchor is attached and so on, and wherein a diameter of the through pores of a first photonic membrane is larger than a diameter of the through pores of a second photonic membrane, the diameter of the through pores of the second photonic membrane is larger than a diameter of the through pores of a third photonic membrane and so on.

According to a third aspect, a method of detecting and identifying target organisms of an analyte comprising non-target organisms and the target organisms, the method comprising flowing the analyte through a photonic membrane with through pores, the through pores having inner walls to which chemical or biological target specific anchors are adapted to be attached, the through pores being distributed on the photonic membrane along multiple regions, through pores pertaining to a first region having inner walls to which a first type of chemical or biological target specific anchor is attached, through pores pertaining to a second region having inner walls to which a second type of chemical or biological target specific anchor is attached, and so on, photonically detecting the target organisms through binding of the target organisms with one or more of the chemical or biological target specific anchor, wherein the photonic membrane is a photonic crystal further comprising a SERS substrate, exposing light on the SERS substrate, the light being out-of-plane to the SERS substrate, exciting plasmon with the light on the SERS substrate, the plasmon coupling the light into molecules of the target organisms, the light being scattered in the target organisms and releasing photons, and photonically identifying the target organisms through distinguishing specific molecular signatures of the target organisms.

According to a fourth aspect, a flow through photonic membrane comprising through pores having inner walls to which chemical or biological target specific anchors are adapted to be attached, the through pores are distributed on the photonic membrane along multiple regions of through pores, through pores pertaining to a first region having inner walls to which a first type of chemical or biological target specific anchor is attached, through pores pertaining to a second region having inner wall to which a second type of chemical or biological target specific anchor is attached, and so on, and a SERS substrate on the photonic membrane, the photonic membrane being a silicon photonic crystal, the SERS substrate being tuned to excite plasmons, wherein the SERS substrate is adapted to couple an out-of-plane optical input into molecules at or near a surface of the SERS substrate, the coupled out-of-plane optical input from the molecules releasing photons.

According to a fifth aspect, a method of fabricating a SERS surface comprising providing a photonic membrane, the photonic crystal comprising through pores having inner walls to which chemical or biological target specific anchors are adapted to be attached, the through pores being distributed on the photonic membrane along multiple regions of through pores, through pores pertaining to a first region having inner walls to which a first type of chemical or biological target specific anchor is attached, through pores pertaining to a second region having inner wall to which a second type of chemical or biological target specific anchor is attached, and so on, providing a substrate on the photonic membrane, etching the substrate, and depositing a colloidal film on the substrate.

Further embodiments of the present disclosure can be found in the written specification, drawings and claims of the present application.

According to an embodiment of the present application, Applicants show a 2D photonic crystal. In particular, a 2D flow through photonic membrane, in which the refractive index periodicity is constituted of alternating layers of bulk silicon and air (well defined channels). This design leads to a dramatic reduction of the detection limit since the device is sensitive to local changes of refractive index in each channel (by opposition to the effective refractive index change that has to occur across the entire porous silicon structure shown on FIG. 3), ultimately leading to single organism detection capabilities for these platforms.

According to a further embodiment, Applicants add a SERS substrate to the 2D photonic crystal, thereby giving it 3D cross-interrogating features whereby the organisms can be further identified using methods based on Raman scattering. Such methods can potentially improve detection sensitivity for molecular species by up to fourteen orders of magnitude relative to unenhanced Raman scattering.

The teachings of the present disclosure provide a viable solution to technology gaps in the Biological Warfare (BW) and Chemical Warfare (CW) detection areas. A real-time capability has been identified to detect, identify, characterize, locate, and warn against BW (and CW) agent threats. The proposed devices and methods combine collection, concentration, detection, and identification of differently sized bio-organisms or chemical agents onto a single platform: a cross-interrogating integrated system of photonic waveguiding silicon membranes and probing for vibrational fingerprints.

The approach of the present disclosure eliminates the current spatial and temporal disconnection between on-field sample collection and laboratory analysis, thus enabling continuous sampling and analysis in gas or liquid phase (e.g., continuous monitoring of air or water). Because of the strong light-confinement properties of photonic crystal microcavities (high quality factor, or high-Q), it is expected that detection is allowed down to a single organism and will only require a very small sensing area (~10-100 $\mu m^2$) and very small amounts of sample (~1-10 fL). In addition, since the membrane allows flow-through, Applicants also expect that much larger volumes of analyte can be accommodated when available, and even further promoted by a three-dimensional staggered filtration architecture. A further advantage of the flow-through geometry according to the present disclosure is that it improves the binding probability of the target organism to the molecular probes anchored on the pore walls.

BRIEF DESCRIPTION OF THE DRAWINGS

FIG. 2A-2C show photon dispersion in a 1D photonic crystal.

DETAILED DESCRIPTION

Figure 1A:
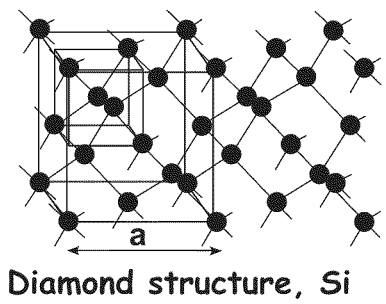
FIG. 1A-1C show electron dispersion in semiconductors.
Figure 1B:
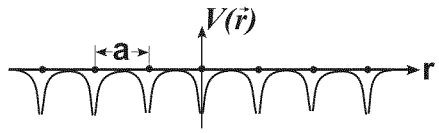
Figure 1C:
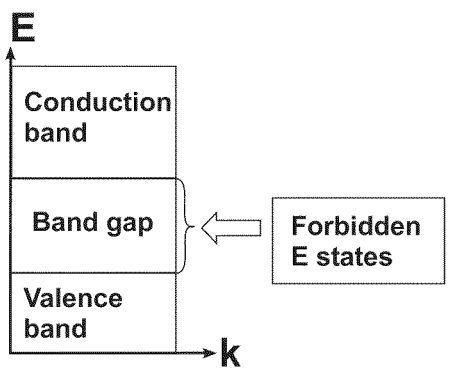
Figure 3:
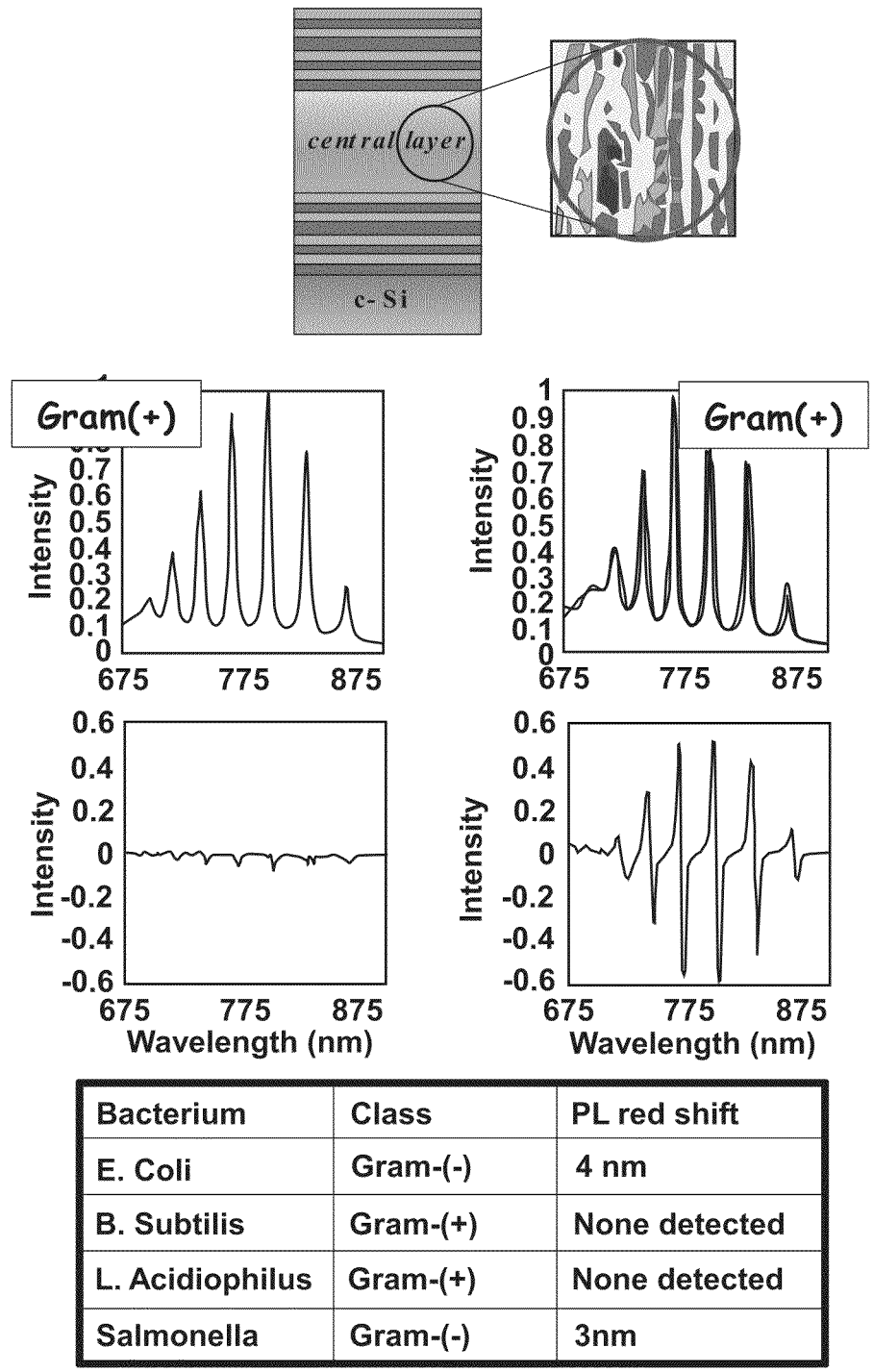
FIG. 3 shows a chemically functionalized 1D photonic crystal for bio-organism detection.
Figure 4:
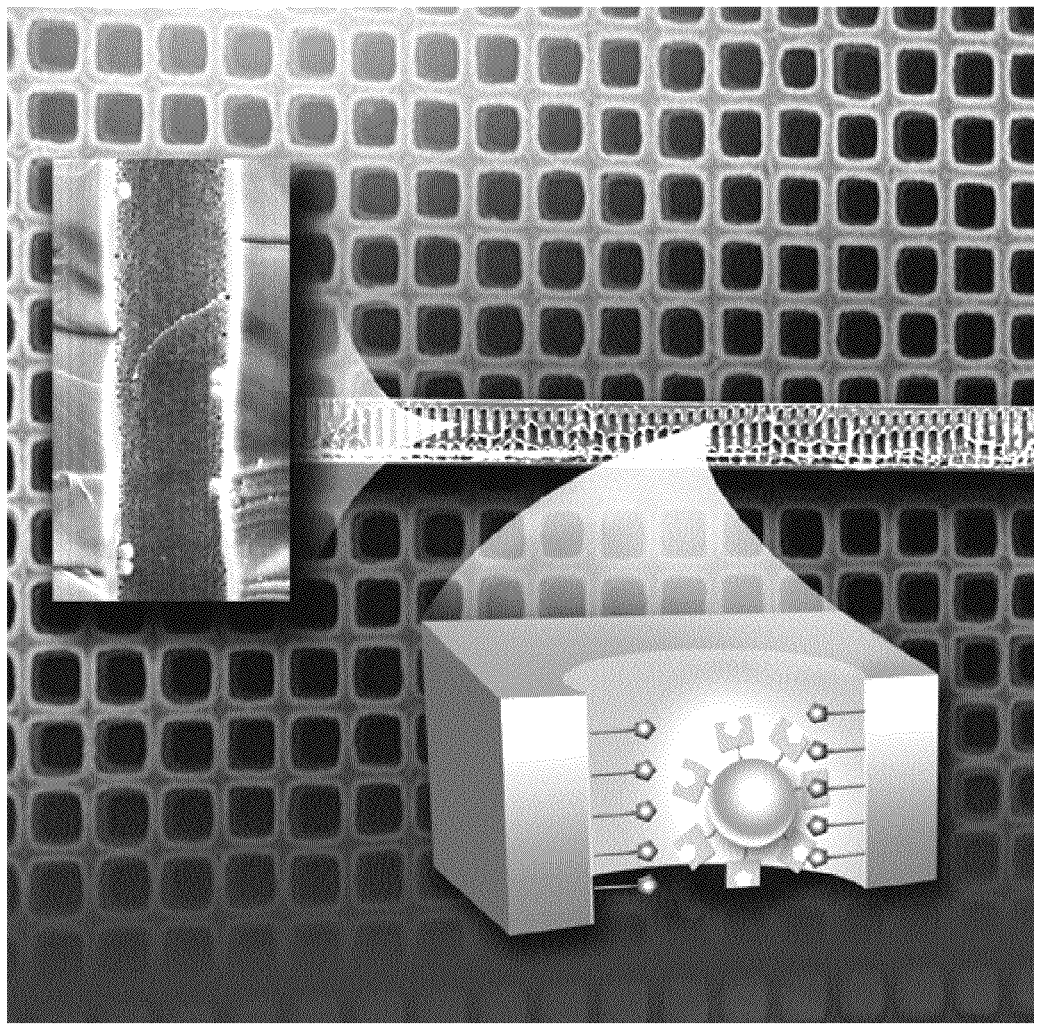
FIG. 4 shows schematic representations of a functionalized membrane and its ability to capture organisms.
Figure 5:
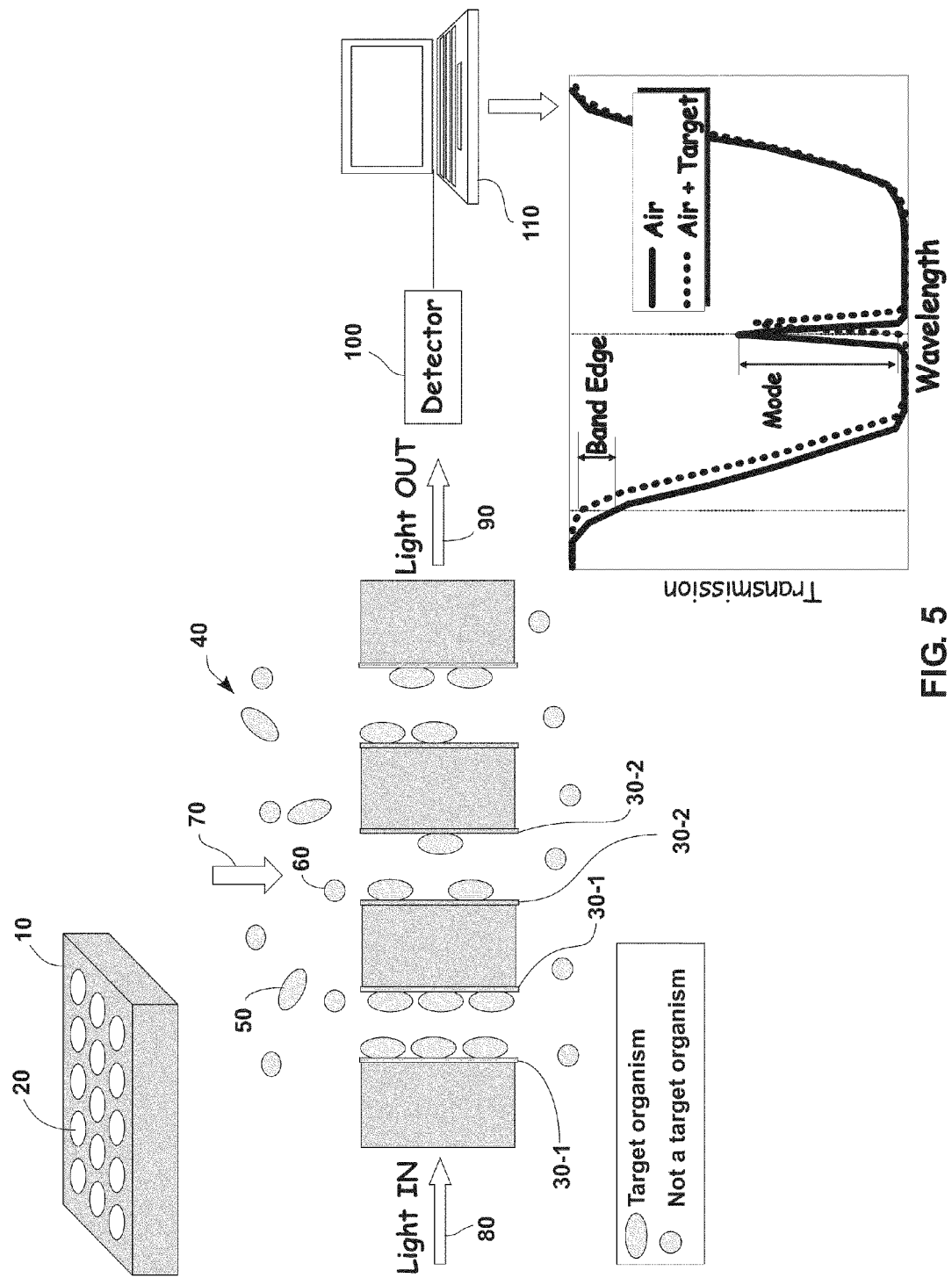
FIG. 5 shows a single-membrane embodiment of a photonic crystal.

FIG. 5 shows a schematic representation of one of the embodiments, where a stand-alone photonic membrane comprising a flow-through silicon crystal (10) is shown both in top perspective view (top portion of the figure) and cross sectional view (middle portion of the figure). The membrane (10) comprises a plurality of channels or pores (20). Each channel or pore (20) has channel walls (30). The channel walls (30) are chemically functionalized with specific probes which allow binding of some chemical and/or biological agents.

According to an embodiment, as better shown in the middle portion of FIG. 5, channel walls (30-1) of a first row of channels can be functionalized with a first probe to be receptive of a first kind of target organism, channels walls (30-2) of a second row of channels can be functionalized with a second probe to be receptive of a second kind of target organism, and so on. Therefore, each time an analyte (40) comprising target organisms (50) and non-target organisms (60) flows (70) through the membrane (10), the target organisms (50) can be detected in view of binding of these organisms on to one or more of the channel walls.

In particular, during the analyte flow (70), light is input (80) in-plane into the photonic membrane (10) and output (90) in-plane from the photonic membrane (10). The output light (90) is detected by a detector (100) and the results evaluated through a data processing system (110). In particular, as shown in the bottom graph of FIG. 5, at a given wavelength, the photonic band gap experienced by light when encountering a point defect translates into different values of light intensity, depending on whether a target is not bound or is bound to the channel walls. Coupling of light into a photonic membrane and further detection is known as "end-fire coupling technique". Membrane pores functionalization and the end-fire coupling technique are known per se from the already mentioned U.S. Pat. No. 7,155,076, which is incorporated herein by reference in its entirety.

According to another embodiment, when a beam of light interacts with some molecule, portions of that light is scattered from the molecule as photons. A majority of the scattered photons are elastically scattered as Rayleigh scattering, where frequency and wavelength of the scattered photons are the same as the incident photons. However, some of the scattered photons are inelastically scattered by excitation as Raman scattering, whereby the frequency is different from that of the incident photons. Such difference in frequency is determined by properties of the molecule with which the beam of light interacts.

Raman scattering contains Stokes and anti-Stokes vibrational information which can be used as fingerprints to identify the type of molecule that the incident light is interacting with. Thus, Raman signal can be used to determine and specifically identify the type of target organism or molecule that is trapped.

By placing the target organism (molecules) that interacts with a light beam on a rough textured metal surface, the Raman scattering effect can be enhanced significantly. Such method of Raman scattering is called Surface Enhanced Raman Scattering (SERS) and has been demonstrated to improve detection sensitivity of molecular species by up to fourteen orders of magnitude.

Figure 6:
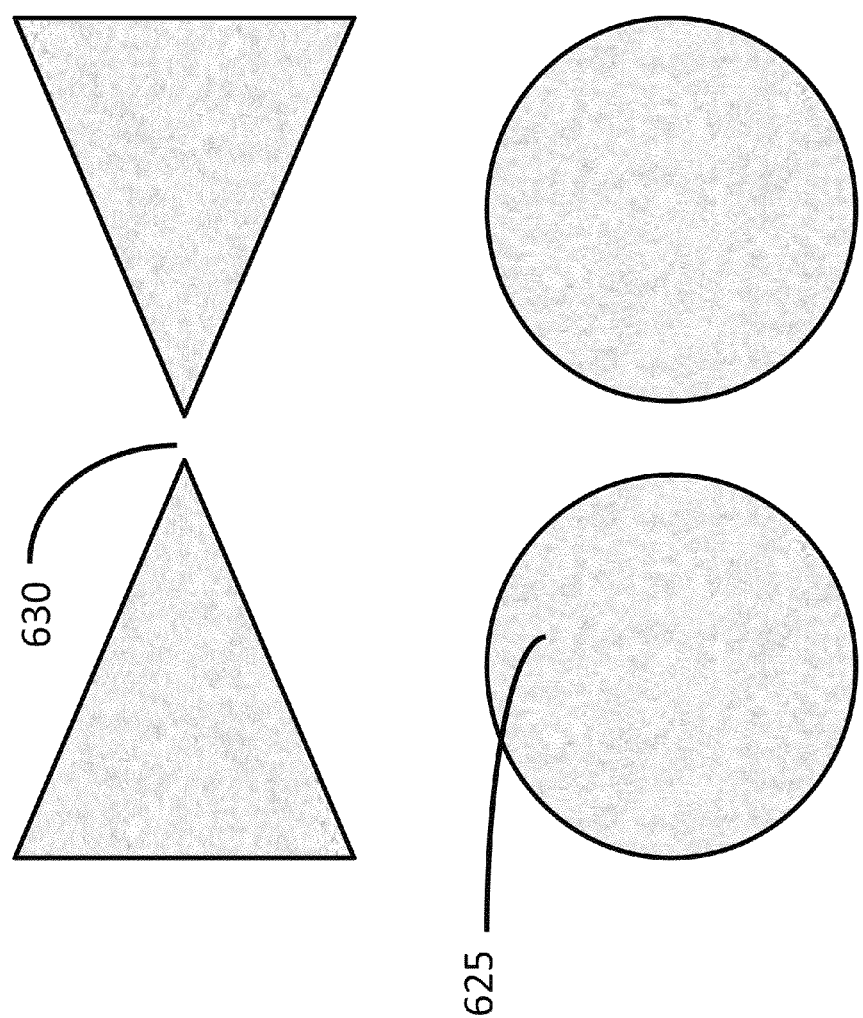
FIG. 6 shows an electric field localization in colloids and sharp points.
Figure 7:
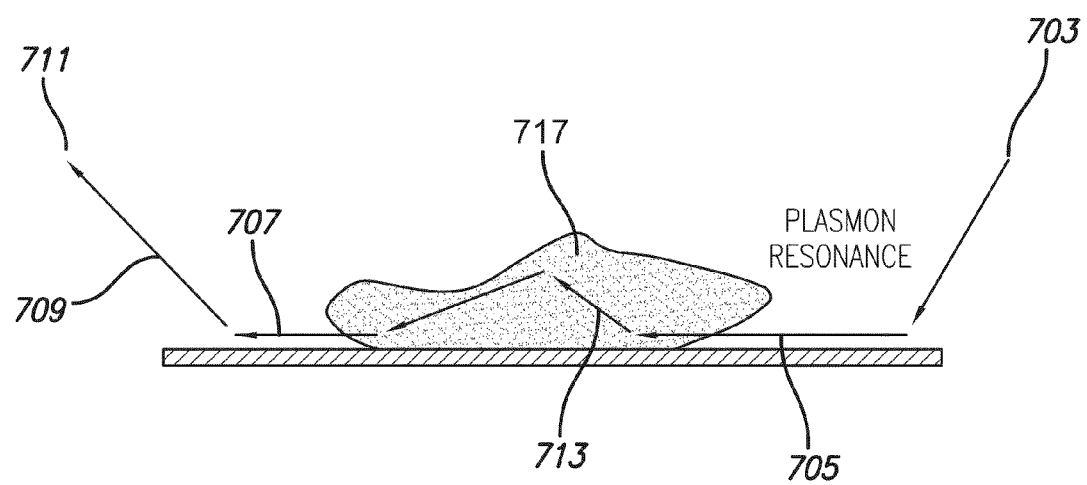
FIG. 7 shows an exemplary Surface Enhanced Raman Scattering (SERS) process.

Such SERS substrate has sharp points (630), as shown in FIG. 6, between colloidal particles (625) in the nano-scale gaps of the textured metal, thus increasing the intensity of light. Such SERS enhancement occurs from plasmon resonances (713), as shown in FIG. 7, which arises when the molecules (717) are close to the metal surfaces as well as when the molecules are in close proximity to clusters of metal atoms. For the sake of simplicity, the terms 'SERS surface' and 'SERS substrate' are used interchangeably herein in the present disclosure.

Plasmons near the metal act as antennas, which assist in coupling light into (705) molecules that are close to the surface and couple out (707) photons, thereby scattering the Raman signal into different directions (709). SERS enhancement occurs as a result of the coupling of scattered light, both into and out of the molecule. Plasmon properties such as wavelength and width of the plasmon resonance depend on geometry, texture and type of metal used for the SERS substrate.

Figure 8A:
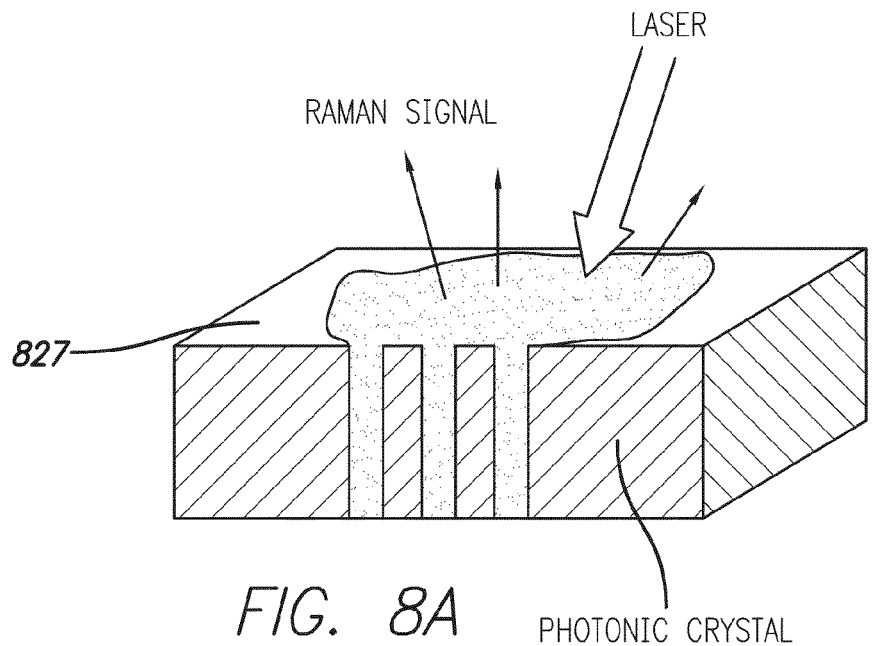
FIG. 8A shows a perspective view of an exemplary photonic crystal SERS substrate with through holes.

According to an embodiment of the present disclosure, FIG. 8A shows the SERS substrate created by coating a surface of a photonic crystal membrane with a metal layer (827) (e.g., gold, silver, or copper) and engineering sub-micron metal cavities on the surface of the metal layer (827). The engineered surface can be created by exploiting different geometrical architectures with fabricated pores (825).

SERS comprises two linked components: an electromagnetic contribution portion and a chemical effect portion. The electromagnetic contribution comes from the increase of the optical intensity in the proximity of sharp points (630) as previously described in FIG. 6, and the chemical effect comes as a result of mixing of an orbital of absorbed molecule and metal atoms. The phenomena mediating the enhanced Raman scattering interaction between the out-of-plane input light source and the target molecule is referred to as a "surface plasmon", which can be viewed as collective charge oscillation at the metal air interface.

Figure 8B:
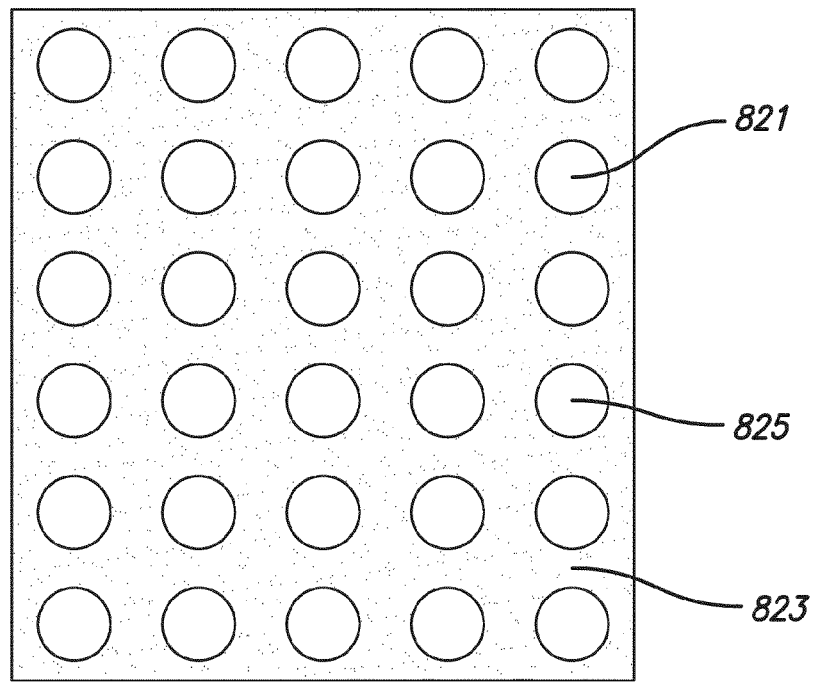
FIG. 8B shows a top view of a SERS substrate with through holes with localized and delocalized plasmons.

Two types of plasmons are supported by the SERS substrate photonic crystal membrane: delocalized (823) plasmons and localized (821) plasmons, as shown in FIG. 8B. The delocalized plasmons (823) are plasmons which are distributed on the metal surface. The localized (821) plasmons are plasmons which are trapped around the through pores of the photonic crystal membrane. The properties of the photonic crystal SERS substrate can be tuned by modifying the size, separation, and orientation of the textured features and cavities. Therefore, the SERS substrate can be utilized for a plurality of types of target organisms. The terms 'SERS substrate' used herein is intended to mean 'SERS substrate photonic crystal membrane'.

As shown in the embodiment of FIG. 5, several different chemical agents or bio-organisms can be collected in a combined way on a single device. This allows analysis to be performed in the field in real time. Moreover, the preparation (both timewise and labor) of the sample to be detected through the membrane of FIG. 5 is minimal, due to PCR-free, label-free whole organism detection technique. Since Raman scattering does not require the target molecule to fluoresce, SERS can be applied to a wide range of target species. Some advantages realized are: 1) enhanced collection due the flow-through design, 2) selectivity provided by surface functionalization with Molecular Recognition Elements such as natural or synthetic antibodies, 3) dramatic sensitivity improvement due to the use of a photonic crystal and to the possibility of engineering high-Q optical microcavities by introducing point and line or region defects, 4) easy implementation of multiplexed bio-organism detection on a chip, and 5) compatibility of interrogation wavelengths with high speed telecommunication systems readily available.

Figure 9:
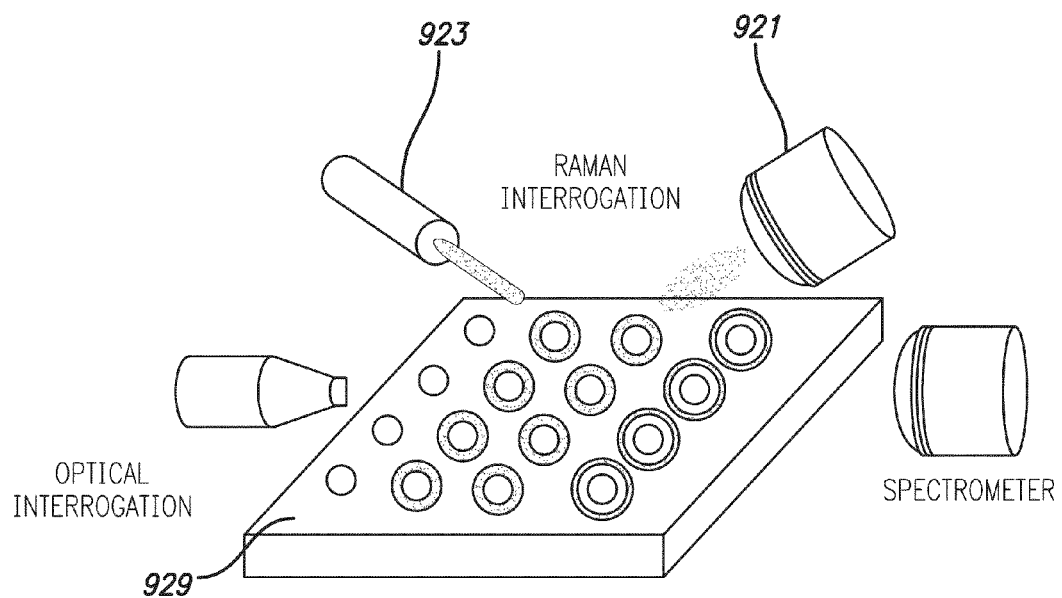
FIG. 9 shows an exemplary cross-interrogation system with the in-plane optical arrangement and an out-of-plane optical arrangement.

FIG. 9 shows a cross-interrogation arrangement showing the SERS substrate (929) and a second light source (923) input out-of-plane to the SERS substrate (929). Accordingly, a spectrometer (921) with a corresponding detector assembly is also arranged such that the spectrometer (921) is adapted to receive the scattered Raman signal (711) shown in FIG. 7. The term 'out-of-plane' as used herein in the present disclosure is intended to be any angle that is not 'in-plane' (e.g., greater than 0 degrees and less than 180 degrees) to the photonic crystal comprising the SERS substrate.

Figure 10A:
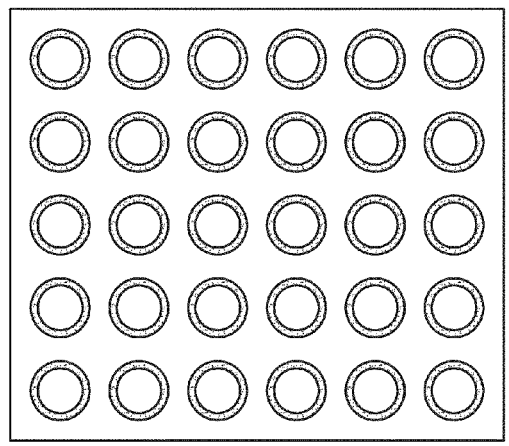
FIG. 10A shows a top view of a SERS substrate.
Figure 10B:
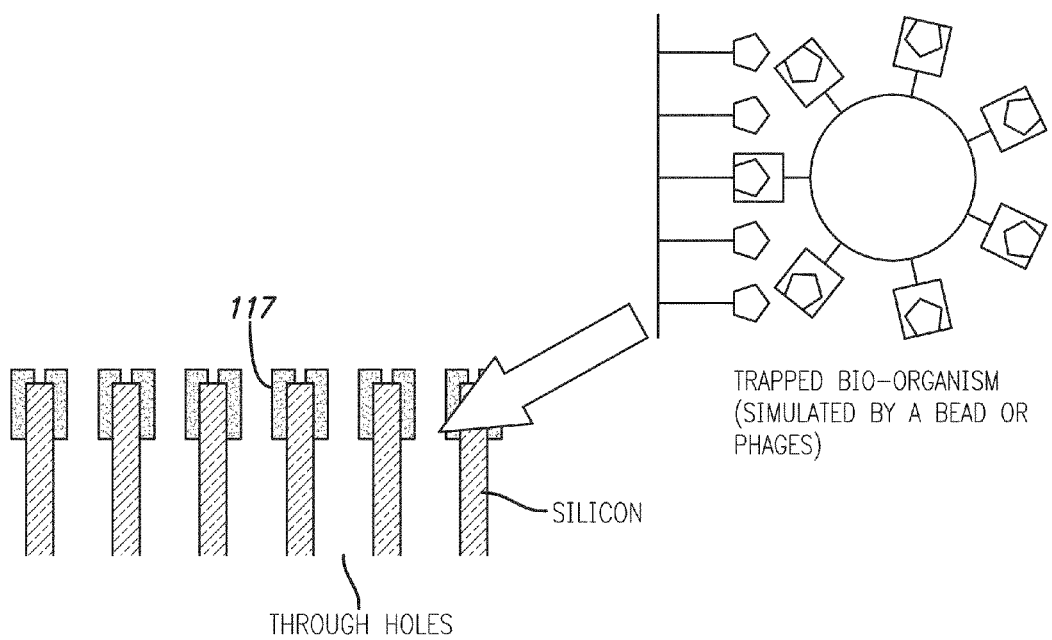
FIG. 10B shows a side view of the SERS substrate of FIG. 10A with metal rings around through holes and an enlarged view of a channel.

When the target organism is trapped in the functionalized channels (117 in FIG. 10) of the photonic crystal SERS substrate, the out-of-plane light is exposed to the surface of the SERS substrate. Such light can be a laser light source but can also be other types of light. When the light is exposed out-of-plane (703) to the surface of the SERS substrate as shown in FIG. 7, the light rays reflect off of the SERS substrate and the photons propagate through the molecules of the analyte. The light that propagates out of the molecules is a Raman signal that further reflects off of the SERS substrate, and scatters in the air. The scattered Raman signal is captured by out-of-plane Raman spectrometers (923).

The Stokes and anti-Stokes vibrational fingerprints from the captured Raman signal can be analyzed using a computer processing system to specifically identify the type of target organism or molecule that is trapped. Such fingerprints for the detection and identification of non-traditional agents and emerging threat agents can be stored in a database. The fingerprint data stored in the database can be used in future analysis to compare against other fingerprints. If the fingerprints match, the computer processing system can easily identify the target organism via PCA (Principal Component Analysis).

The combination cross-interrogation of optically waveguiding along with the surface enhanced Raman scattering allows for improved organism detection and identification. Such cross-interrogation methods can be performed concomitantly or separately. However, should the cross-interrogation be performed concomitantly, the wavelengths of the light sources should comprise different wavelength so as to prevent the computer processing systems from confusing the light inputs.

Figure 11:
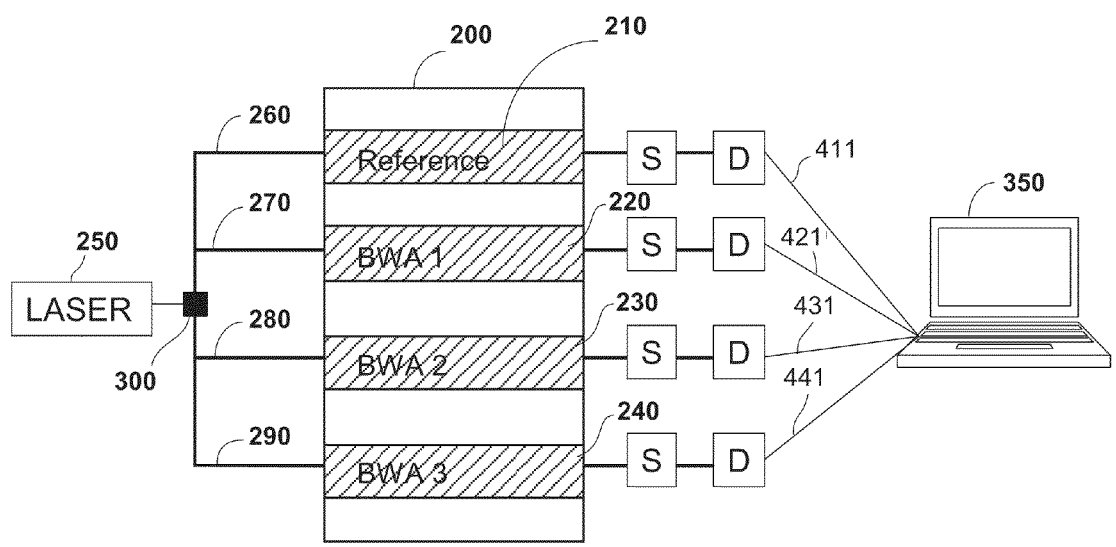
FIG. 11 shows a single-membrane embodiment with light input, detection and processing architecture.

FIG. 11 shows a further embodiment. As shown in the top view of the figure, a photonic membrane (200) comprises a plurality of regions (210, 220, 230, 240), each region including a plurality of through holes (as later shown in FIG. 12), grouped into a plurality of regions, e.g., lines.

Figure 12:
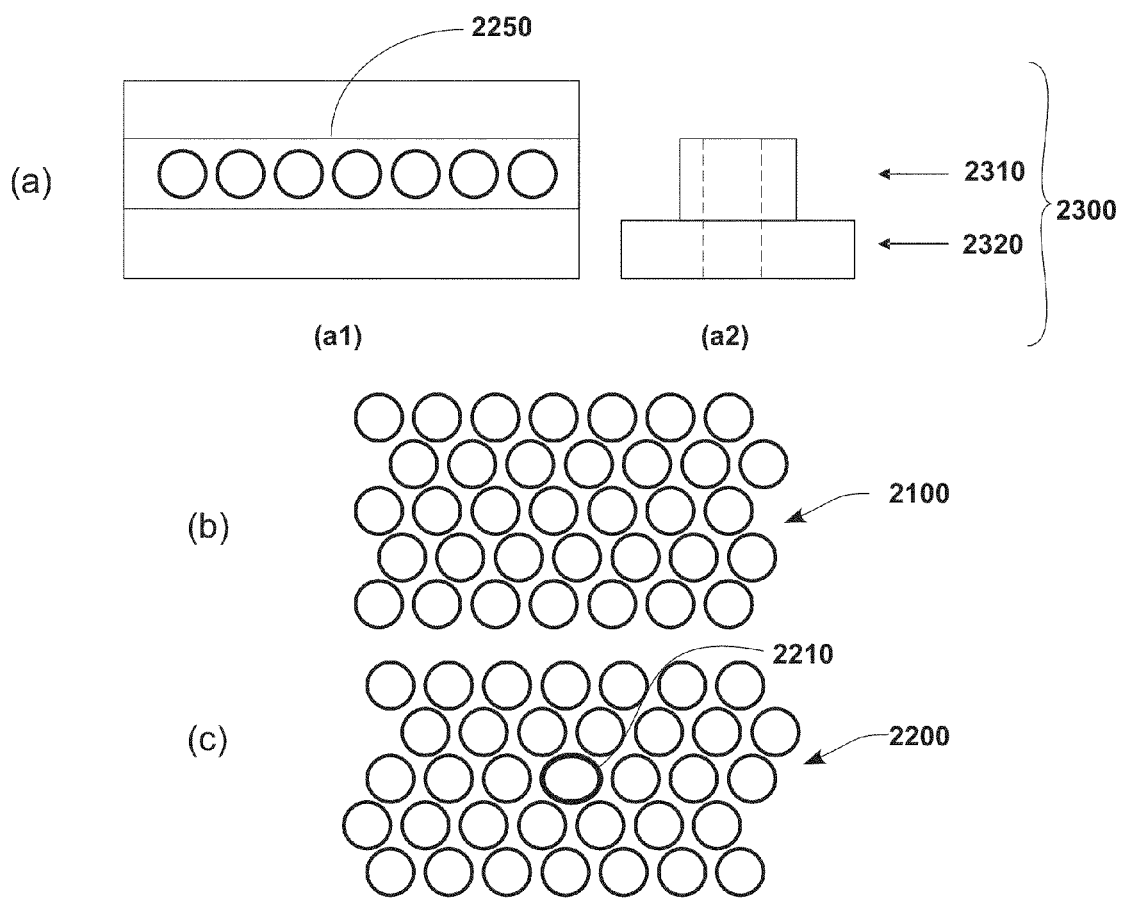
FIG. 12 shows some possible through hole arrangements for the embodiment of FIG. 11.

FIG. 12 shows three possible arrangements for each region (210, 220, 230, 240) as previously shown in FIG. 11. In the arrangement (a) of FIG. 12, the through holes are distributed around a single region, e.g., a line. In particular, section (a1) shows a top view of the membrane and section (a2) shows a bottom view of the membrane. Each line of pores (2250) has a ridge geometry (2300), comprised of a waveguide section (2310) and a cladding section (2320). In the arrangement (b) of FIG. 12, a region can comprise a perfect photonic crystal (2100) including an array of through pores. In the arrangement (c) of FIG. 12, a region can include a photonic crystal (2200) comprising an array of pores and a defect (2210). The defect (2210) can be, for example, a pore with a different diameter, or a removed pore.

Similar to that explained in FIG. 5, each region (210, 220, 230, 240) of FIG. 11 can be functionalized in a different manner. The first line or row (210) can be a reference row, where the channel walls are not functionalized. The second row (220) can have channel walls functionalized for bonding with a first Bio-Warfare Agent BWA1 (it could also be a chemical agent). The third row (230) can have channel walls functionalized for bonding with a second agent BWA2, and so on. A light source (250), e.g., a continuous wave laser diode source, is split into a plurality of optic fibers (260, 270, 280, 290) by way of a splitter (300). One or more output fibers can send the signal to a compact multi-channel spectrometer, represented in FIG. 11 as a plurality of units (S). A plurality of detecting units (D), each corresponding to a respective row, can be located downstream of the membrane (200). A processor (350), e.g., a laptop computer, can compare the signal of each functionalized line (421, 431, 441) to the un-functionalized reference line (411) by way of differential measurement in order to suppress noise and interferences, and then analyze the data to allow bio-organism identification. In case a compact embodiment is desired, the spectrometer can be powered by the laptop batteries. In such embodiment, the size and weight of the overall system could be a few cubic feet and below 2 pounds. Future designs can provide an arrangement in which the system is fully integrated on a single platform compatible with CMOS readout circuitry designed for lab-on-a-chip applications.

With reference to the embodiments of FIGS. 11-12, the person skilled in the art will understand that each region (210, 220, 230, 240) of FIG. 11 can have any one of the arrangements (a), (b), (c) shown in FIG. 12. Also, each region can have through pores having a different diameter or shape than the through pores of other regions.

The transmission of light through the photonic crystal can be recorded before and after binding of the organisms using the end-fire technique described with reference to FIG. 5. In particular, upon binding of the bio-organisms in the channels of the flow-through photonic crystal, the refractive index of the channels will increase and the transmission curve will shift, where the amplitude of the shift is dependent on the channel volume occupied by simulated bio-organisms. Comparison of the transmission curves recorded before and after binding of various concentrations of antigen-coated beads (for both virus and bacteria size regimes) can be used to determine the experimental detection limit in both dry and aqueous phase.

The membrane in accordance with the embodiments of FIGS. 5 and 11 can be operated according to two different approaches. In a first mode of operation, a white light source is used in combination with a spectrometer to evaluate the wide band gap of the membrane (of the order of hundreds of nanometers). In this way, a full spectral trace of the photonic band gap is provided. Such spectral trace can be used for general device characterization and for sensing in perfectly periodic photonic crystals, in which the binding of the target in a pore is transduced by a spectral shift of the broad band edge feature. In a second mode of operation, a monochromatic light, e.g., a compact laser is used in combination with the detectors (e.g., high sensitivity detectors possibly integrated with narrow band filters) placed at the output, to measure narrow resonances (expected to be a few nm) and relative changes in the intensity of the transmitted monochromatic light induced by inserted defects. Usually, this second mode of operation is more sensitive and needs less power.

A further embodiment of the present disclosure is shown in FIG. 13, where vertically stacked photonic membranes with various channel sizes are shown. Throughout the following description of FIG. 13, reference will be made to through pores having an arrangement similar to the arrangement (a) of FIG. 12. However, the person skilled in the art will understand that also through pores according to the arrangements (b) and (c) of FIG. 12 can be provided. Turning to the embodiment of FIG. 13, such figure shows, by way of example, three vertically stacked membranes (400, 500 and 600). Each membrane comprises a row of reference pores (410, 510, 610) and a plurality of functionalized rows (420, 520, 620; 430, 530, 630; 440; 540; 640). The diameter of the pores of membrane (500) is smaller than the diameter of the pores of membrane (400). Similarly, the diameter of the pores of membrane (600) is smaller than the diameter of the pores of membrane (500). According to an embodiment, a first line (410) of through pores of a first photonic membrane (400) is in spatial correspondence with a first line (510) of through pores of a second photonic membrane (500). Similarly, a second line (420) of through pores of the first photonic membrane (400) can be in spatial correspondence with a second line (520) of through pores of the second photonic membrane (500) and so on.

As shown in FIG. 13, and similarly to that previously shown in FIG. 11, each membrane (400, 500, 600) is connected to an input light source (700, 701, 702, respectively) by way of input fibers (710, 720, 730, 740). On the output side, a multichannel detector (800) is provided. The flow of the analytes is from the top (810) to the bottom (820). According to an embodiment, one detector per membrane is provided, in view of the fact that the wavelength is different for each membrane of the stack of membranes. In particular, the wavelength should match the photonic band gap, which itself depends on the size of the pores and the period of their arrangement. The detector can be a multichannel detector so that it can receive multiple inputs (coming from the multiple lines) for each membrane. In addition, to support the cross-interrogation embodiment of the present disclosure, each of the plurality of the vertically stacked photonic membranes can also be arranged with the second out-of-plane light source input and the corresponding spectrometer/detector assemblies.

In this way, a progression of pore diameters, starting, for example, from large bacteria-sized channels and progressively reduced, for example, to virus size, is obtained. Such geometry also reduces the clogging probability while allowing multiplexing. Moreover, the size of the organism can be determined vertically and chemical composition of the coat can be detected horizontally (for each size range, various antibodies can be anchored on parallel channel rows). The structure of FIG. 13 can be used, for example, for full bio-organism identification, or for signature generation on unknown threat organisms.

The number of pores per line is subject to competing conditions: on one side, more pores provide a long range periodicity and, therefore, a well defined photonic band gap; on the other side, more pores also imply a longer distance for the photons to travel and, therefore, a higher probability of losses. Point defects can also be inserted in each row to engineer and control modes in the photonic band gap.

Figure 13:
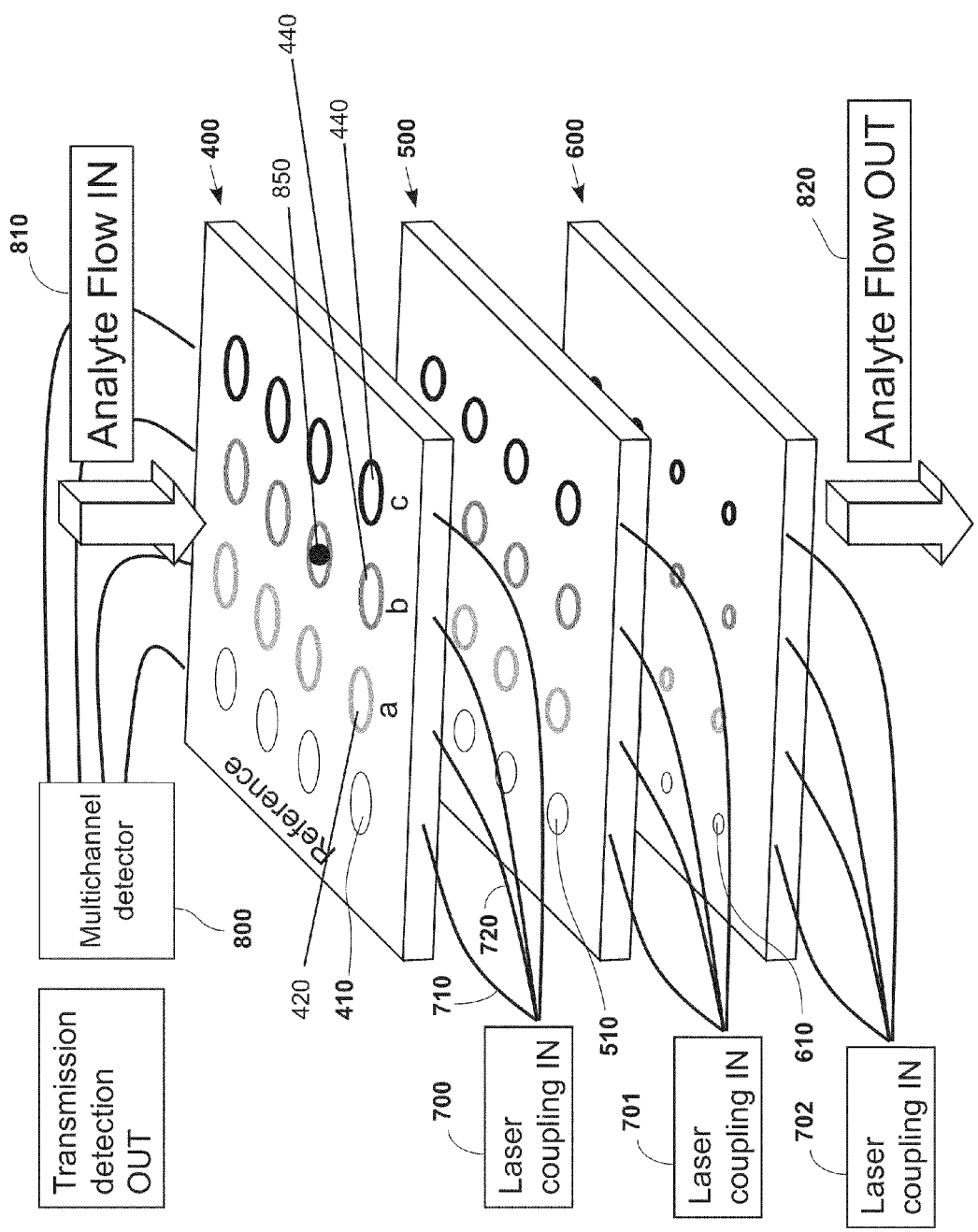
FIG. 13 shows a multiple-membrane embodiment of the present disclosure.

If a bio-organism (represented by the bead (850) in FIG. 13) binds in the structure, the location of the binding will provide information on the organism size and bio-organism family. For example, the bio-organism (850) is bound on membrane (400 in FIG. 13), which would mean, for example, that is a bacterium with a 200 nm diameter; and is bound on row (430), which would mean that it binds on the antibody provided on the surface walls of pores (430).

The wavelength of the light used in the embodiments of the previous figures can also be an ultraviolet (UV) or near-infrared (IR) frequency.

Each photonic waveguide slab or membrane can be made, for example, of silicon or other materials such as SiONy, SiOx, SiC, GaN, PbTe and, more generally, oxides, III-V or II-VI semiconductors, and polymers. Various interrogation wavelengths can be used across the device, as already explained above. In particular, smaller pore sizes mean a photonic band gap at a lower wavelength. As also mentioned before, a broad source can be used to record the entire band gap transmission, while a single wavelength can be used to interrogate specific modes in the photonic band gap. The device can be used for biological (e.g., bacteria, viruses, toxin) and chemical sensing.

Figure 14:
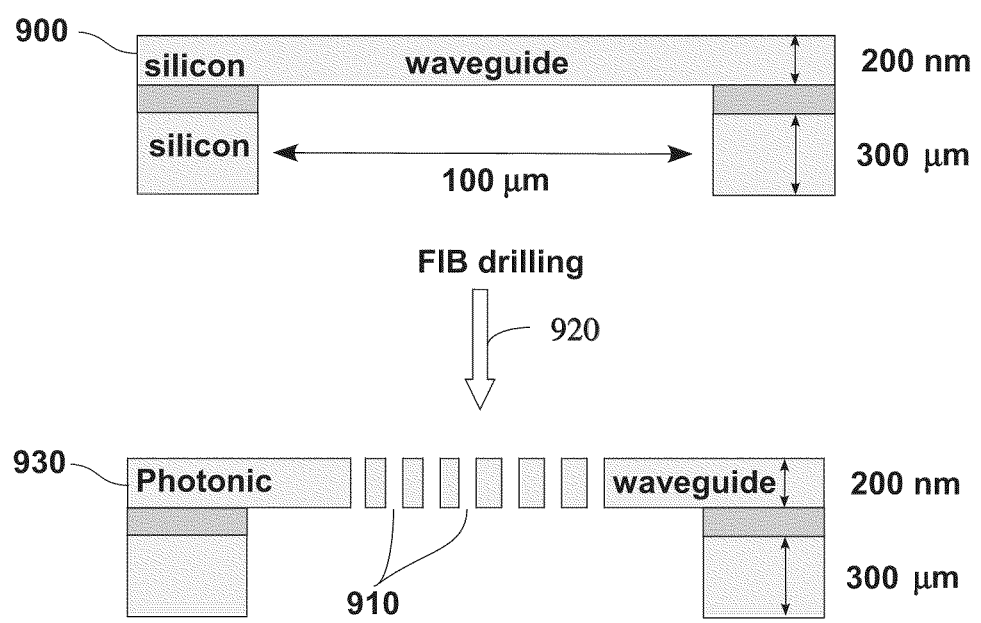
FIG. 14 shows an exemplary method of fabrication of the flow-through membrane.

FIG. 14 shows an exemplary method of fabrication of the membrane of the present disclosure. In particular, silicon on insulator (SOI) wafers (having, for example, a device layer thickness of 200 nm) can i) be optionally coated with silicon nitride, ii) patterned by standard photolithography techniques, and iii) etched (e.g., by deep reactive ion etching, DRIE) in order to obtain free-standing 200 nm thick silicon waveguides (900) which will allow, for example, a single mode propagation at 1.55 μm. Alternatively, nanoimprinting can also be used to fabricate the membrane. A periodic pattern of through channels (910) can then be drilled on the waveguide by methods such as electron beam lithography with dry chemical etching, or focused ion beam (FIB) (920), to open a photonic band gap into the waveguide and convert the silicon waveguide (900) into a flow-through photonic silicon membrane (930). With the FIB technique there is no limitation on the geometry of the drilled pattern or on the dimensions of the channels (910) above a 1:10 (channel diameter:membrane thickness) aspect ratio. Moreover, for the small patterns contemplated by the present disclosure, FIB constitutes a fast (under an hour for an array of 10×10 channels) and versatile technique as no mask has to be designed. A change in the pattern to test theoretical predictions can be achieved in a matter of minutes at no cost by reprogramming the drilling sequence, while it would take days and money to design new masks when using lithography techniques. Moreover, FIB drilling gives access to channel diameters ranging from nanometers to many microns, while standard lithography is limited to a few hundreds of nanometers.

Figure 15:
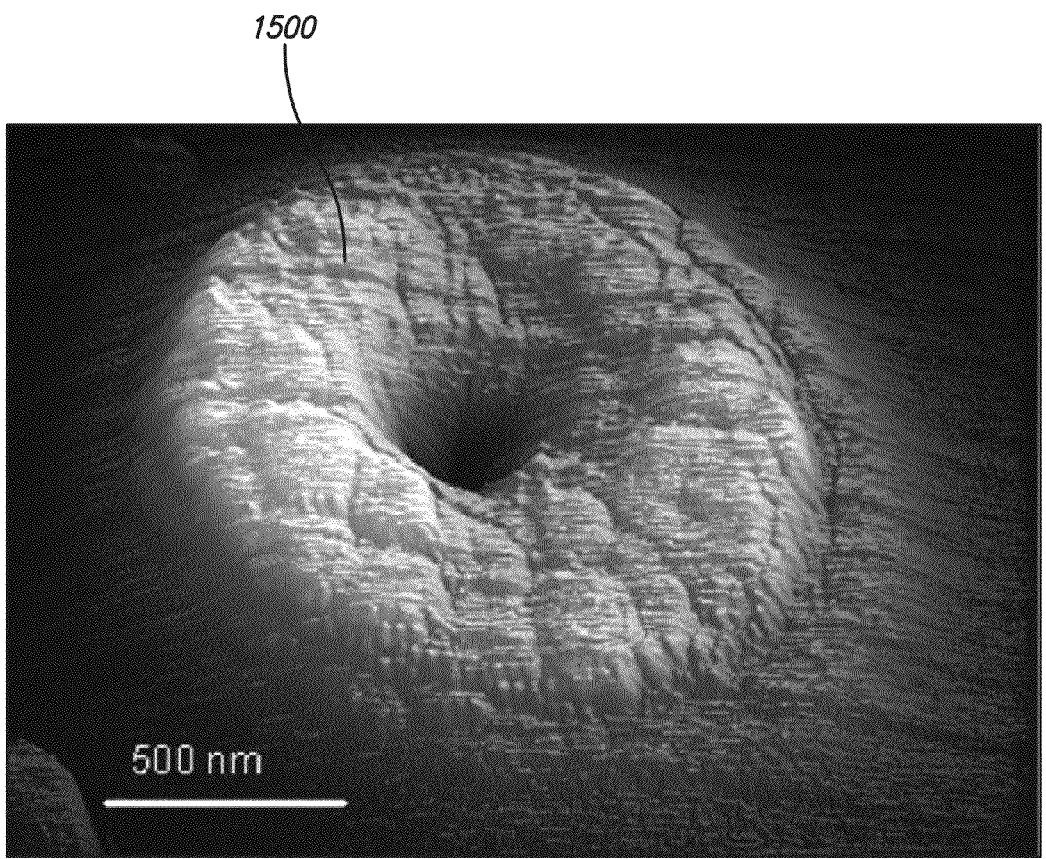
FIG. 15 shows an image of a single through hole drilled by focused ion beam (FIB) surrounded by a ring of oxide.

According to another embodiment of the present disclosure, in case of the delocalized plasmon scenario, a single metal or metal-dielectric colloidal film (e.g., silver, gold, or copper) can be deposited on the photonic crystal substrate (e.g., silicon). In case of the localized plasmon scenario, once the through channels (910) are drilled by FIB (920), metal rings (117, 1500) shown in FIGS. 10B and 15 respectively, could be deposited around the through channels (910) using local FIB metal deposition, similarly to those methods used for depositing tetraethyl orthosilicate (TEOS) rings around a single channel (see Nilsson, J. R. I. Lee, T. V. Ratto and S. E. Létant (2006), "Localized Functionalization of Single Nanopores", Advanced Materials 18, 427-431). In an alternative method for depositing the metal rings (1500), beads can be used to template the ring fabrication (see Larsson, E. M.; Alegret, J.; Kall, M.; Sutherland, D. S., "Sensing Characteristics of NIR Localized Surface Plasmon Resonances in Gold Nanorings for Application as Ultrasensitive Biosensors", Nano Letters 2007, 7, (5), 1256-1263). The metal pattern of the metal ring can be different from the channel pattern created in the dielectric, thereby offering flexibility as well as the opportunity for localized signals. Although not a limitation, one of the advantages of the metal ring geometry of the SERS substrate is that the SERS can locally operate at the mouth of the channel to cause minimal impact on the optical transmission properties of the photonic band gap structure.

Accordingly, what has been shown are photonic membranes for detection and plasmonic identification of biological and/or chemical organisms, and related detection methods. While the membranes and methods have been described by means of specific embodiments and applications thereof, it is understood that numerous modifications and variations could be made thereto by those skilled in the art without departing from the spirit and scope of the disclosure. It is therefore to be understood that within the scope of the claims, the disclosure may be practiced otherwise than as specifically described herein.

The examples set forth above are provided to give those of ordinary skill in the art a complete disclosure and description of how to make and use the embodiments of the methods and systems for Raman and optical cross-interrogation in flow-through silicon membranes of the disclosure, and are not intended to limit the scope of what the inventors regard as their disclosure. Modifications of the above-described modes for carrying out the disclosure may be used by persons of skill in the art, and are intended to be within the scope of the following claims. All patents and publications mentioned in the specification may be indicative of the levels of skill of those skilled in the art to which the disclosure pertains. All references cited in this disclosure are incorporated by reference to the same extent as if each reference had been incorporated by reference in its entirety individually.

It is to be understood that the disclosure is not limited to particular methods or systems, which can, of course, vary. It is also to be understood that the terminology used herein is for the purpose of describing particular embodiments only, and is not intended to be limiting. As used in this specification and the appended claims, the singular forms "a", "an", and "the" include plural referents unless the content clearly dictates otherwise. The term "plurality" includes two or more referents unless the content clearly dictates otherwise. Unless defined otherwise, all technical and scientific terms used herein have the same meaning as commonly understood by one of ordinary skill in the art to which the disclosure pertains.

A number of embodiments of the disclosure have been described. Nevertheless, it will be understood that various modifications may be made without departing from the spirit and scope of the present disclosure. Accordingly, other embodiments are within the scope of the following claims.

The invention claimed is:

1. A combination photonic detection and identification system comprising:
   a photonic membrane with through pores, the through pores having inner walls to which chemical or biological target specific anchors are adapted to be attached;
   a first optical input to the photonic membrane, the first optical input in-plane with the photonic membrane;
   a first optical output detecting arrangement arranged in-plane with the photonic membrane;
   a second optical input to the photonic membrane, the second optical input arranged out-of-plane to the photonic membrane; and
   a second optical output detecting arrangement arranged out-of-plane to the photonic membrane,
   wherein the photonic membrane is a silicon photonic crystal further comprising a SERS substrate comprising a surface coated with metal rings facing the second optical input and the second optical output detecting arrangement, the SERS substrate being tuned to excite plasmons, wherein the SERS substrate is adapted to couple the second optical input into molecules at or near a surface of the SERS substrate, the coupled second optical input from the molecules releasing photons, and wherein the metal rings are in correspondence of entrances of the through pores, and
   wherein the through pores are distributed on the photonic membrane along multiple regions of through pores, wherein through pores pertaining to one region have inner walls to which one type of chemical or biological target specific anchor is attached, and wherein through pores pertaining to another region have inner walls to which another type of chemical or biological target specific anchor is attached.

2. The system of claim 1, wherein the SERS substrate comprises sharp points of textured metals.

3. The system of claim 1, wherein the SERS substrate comprises nano-scale gaps between colloidal particles.

4. The system of claim 1, wherein the first optical input to the photonic membrane comprises a plurality of optical input lines, and the first optical output detecting arrangement comprises a plurality of detectors, one for each optical input line and a detector for each region of through pores.

5. The system of claim 4, wherein measurement of an in-plane optical detection output of the photonic detection system occurs differentially, by subtraction of a detection output of an additional region of through pores from a detection output of each region of through pores.

6. The system of claim 5, wherein measurement of an out-of-plane optical detection output of the photonic detection system occurs by probing for vibrational fingerprints of chemical or biological target.

7. The system of claim 1, wherein the second optical input is a laser light.

8. The system of claim 1, wherein the second optical output detecting arrangement further comprises one or more spectrometers and one or more detector assemblies adapted to measure scattered light from the SERS substrate.

9. The system of claim 1, wherein the first optical output detecting arrangement is a multichannel detector.

10. The system of claim 1, wherein the first optical output detecting arrangement is connected with a processing unit downstream of the photonic membrane.

11. The system of claim 10, wherein the processing unit is a portable computer.

12. The system of claim 1, wherein the multiple regions of through pores are shaped differently from each other.

13. The system of claim 1, wherein each region of through pores is selected from the group consisting of: a line of through pores with a ridge geometry, a perfect photonic crystal comprising an array of through pores, and a photonic crystal comprising an array of through pores and a defect.

14. The system of claim 13, wherein the defect is selected from the group consisting of: a pore with a different diameter or shape than the remaining through pores of the array, and a removed pore.

15. The system of claim 4, wherein the first optical input comprises a light from a laser that is split into a plurality of optic fibers by way of a splitter.

16. The system of claim 5, wherein the through pores of the additional region are unfunctionalized.

17. A combination photonic detection and identification system comprising:
   a plurality of photonic membranes stacked on each other, each photonic membrane having through pores, the through pores having inner walls to which chemical or biological target specific anchors are adapted to be attached;
   a first optical input arrangement, the first optical input arrangement in-plane with the plurality of photonic membranes;
   a first optical output detecting arrangement connected in-plane with the plurality of photonic membranes,
   a second optical input, the second optical input arranged out-of-plane to the plurality of photonic membranes; and
   a second optical output arrangement connected out-of-plane to the plurality of photonic membranes;
   wherein the plurality of photonic membranes are silicon photonic crystals,
   wherein the plurality of photonic membranes comprises a SERS substrate comprising a surface coated with metal rings facing the second optical input and the second optical output arrangement, the SERS substrate being tuned to excite plasmons, wherein the SERS substrate is adapted to couple the second optical input into molecules at or near a surface of the SERS substrate, the coupled second optical input from the molecules releasing photons,
   wherein the through pores are distributed on each of the photonic membranes along multiple regions of through pores, wherein through pores pertaining to one region have inner walls to which one type of chemical or biological target specific anchor is attached, and wherein through pores pertaining to another region have inner walls to which another type of chemical or biological target specific anchor is attached, and wherein the metal rings are in correspondence of entrances of the through pores, and wherein a diameter of the through pores of the plurality of photonic membranes decreases from one photonic membrane to another photonic membrane.

18. The system of claim 17, wherein the SERS substrate comprises sharp points of textured metals.

19. The system of claim 18, wherein measurement of an out-of-plane optical detection output of the photonic detection system occurs by probing for vibrational fingerprints of chemical or biological target.

20. The system of claim 17, wherein each region of through pores is selected from the group consisting of: a line of through pores with a ridge geometry, a perfect photonic crystal comprising an array of through pores, and a photonic crystal comprising an array of through pores and a defect.

21. The system of claim 20, wherein the defect is selected from the group consisting of: a pore with a different diameter or shape than the remaining through pores of the array, and a removed pore.

22. A system comprising
a flow through photonic membrane comprising through pores and a SERS substrate comprising a surface coated with metal rings;
an out-of-plane optical input arrangement facing said surface; and
an out-of-plane optical output arrangement facing said surface,
wherein
the through pores have inner walls to which chemical or biological target specific anchors are adapted to be attached, the through pores being distributed on the photonic membrane along multiple regions of through pores, wherein through pores pertaining to one region have inner walls to which one type of chemical or biological target specific anchor is attached, and wherein through pores pertaining to another region have inner walls to which another type of chemical or biological target specific anchor is attached; and
the photonic membrane being is a silicon photonic crystal, the SERS substrate being tuned to excite plasmons, wherein the SERS substrate is adapted to couple an out-of-plane optical input from the out-of-plane optical input arrangement facing said surface into molecules at or near said surface and to feed an out-of-plane optical output to the out-of-plane optical output arrangement facing said surface, the coupled out-of-plane optical input from the molecules releasing photons and wherein the metal rings are in correspondence of entrances of the through pores.

23. The system of claim 22, wherein the SERS substrate is a colloidal film.

24. The system of claim 23, wherein the colloidal film is selected from the group consisting of: gold, silver, and copper.

25. A method of using a photonic membrane, the photonic membrane comprising:
through pores having inner walls to which chemical or biological target specific anchors are adapted to be attached, the through pores are distributed on the photonic membrane along multiple regions of through pores, wherein through pores pertaining to one region have inner walls to which one type of chemical or biological target specific anchor is attached, and wherein through pores pertaining to another region have inner walls to which another type of chemical or biological target specific anchor is attached; and
a SERS substrate comprising a surface coated with metal rings on the photonic membrane, the photonic membrane being a silicon photonic crystal, the SERS substrate being tuned to excite plasmons, wherein the SERS substrate is adapted to couple an out-of-plane optical input from an out-of-plane optical input arrangement facing said surface into molecules at or near said surface and to feed an out-of-plane optical output to an out-of-plane optical output arrangement facing said surface, the coupled out-of-plane optical input from the molecules releasing photons and wherein the metal rings are in correspondence of entrances of the through pores, the method comprising:
inputting one or more light sources in-plane to the photonic membrane;
feeding a corresponding in-plane output from the photonic membrane to a spectrometer arrangement;
exposing the SERS substrate with a second light source, the second light source being said out-of-plane optical input arrangement; and
feeding a corresponding Raman output from the SERS substrate to a second spectrometer arrangement, the second spectrometer arrangement being said out-of-plane optical output arrangement.

* * * * *